(12) United States Patent
Gunaratne et al.

(10) Patent No.: US 9,192,622 B2
(45) Date of Patent: Nov. 24, 2015

(54) MICRORNA-130A,B AS A TUMOR SUPPRESSOR AND SENSITIZING AGENT FOR CHEMOTHERAPY

(75) Inventors: Preethi H. Gunaratne, Houston, TX (US); Ashley L. Benham, Kingwood, TX (US); Matthew L. Anderson, Houston, TX (US)

(73) Assignee: University of Houston, Houston, TX (US)

( * ) Notice: Subject to any disclaimer, the term of this patent is extended or adjusted under 35 U.S.C. 154(b) by 0 days.

(21) Appl. No.: 13/437,251

(22) Filed: Apr. 2, 2012

(65) Prior Publication Data

US 2013/0089597 A1    Apr. 11, 2013

Related U.S. Application Data

(60) Provisional application No. 61/516,239, filed on Mar. 31, 2011.

(51) Int. Cl.
| | | |
|---|---|---|
| *A61K 48/00* | (2006.01) |
| *A61K 31/713* | (2006.01) |
| *A61K 31/7105* | (2006.01) |
| *A61K 33/24* | (2006.01) |
| *A61K 45/06* | (2006.01) |
| *C12Q 1/68* | (2006.01) |
| *A61K 9/127* | (2006.01) |
| *C12N 15/113* | (2010.01) |

(52) U.S. Cl.
CPC .............. *A61K 31/713* (2013.01); *A61K 9/127* (2013.01); *A61K 31/7105* (2013.01); *A61K 33/24* (2013.01); *A61K 45/06* (2013.01); *C12N 15/113* (2013.01); *C12Q 1/6886* (2013.01); *C12N 2310/141* (2013.01); *C12N 2320/31* (2013.01); *C12Q 2600/178* (2013.01)

(58) Field of Classification Search
None
See application file for complete search history.

(56) References Cited

U.S. PATENT DOCUMENTS

| 2008/0076674 | A1 | 3/2008 | Litman et al. | |
|---|---|---|---|---|
| 2010/0113290 | A1 | 5/2010 | Klass et al. | |
| 2011/0313025 | A1* | 12/2011 | Brown et al. | ................ 514/44 A |

FOREIGN PATENT DOCUMENTS

| EP | 2283846 A1 | 2/2011 |
|---|---|---|
| EP | 2290074 A2 | 3/2011 |
| WO | 2009080437 A1 | 7/2009 |

OTHER PUBLICATIONS

Jaarsveld et al. (International Journal of Biochem & Cell Bio 2010, 1282-1290).*
Sorrentino et al. (Gynecologic Oncology 2008, 478-486).*
Cochrane et al. (Mol Cancer Ther 2009, 1055-1066).*
Yang, C et al. Epigenetic silencing of miR-130b in ovarian cancer promotes the development of multidrug resistance by targeting colony-stimulating factor 1. Gynecologic Oncology, 2011; vol. 124: pp. 325-334; abstract; figure 5.
Sorrentino, A et al. Role of microRNAs in drug-resistant ovarian cancer cells. Gynecologic Oncology, 2008; vol. 111: pp. 478-486; abstract; table.

* cited by examiner

*Primary Examiner* — Kimberly Chong
(74) *Attorney, Agent, or Firm* — Benjamin Aaron Adler

(57) ABSTRACT

The present invention provides a method of improving a therapeutic response to a cancer treatment, in a subject, the method comprising administering an effective amount of an agent that enhances the expression of microRNA-130 or an agent that mimics the effects of microRNA-130. Further provided is a method of treating a cancer in a subject in need of such treatment comprising the step of administering an effective amount of a microRNA-130 or an agent that enhances the expression of microRNA-130.

12 Claims, 12 Drawing Sheets

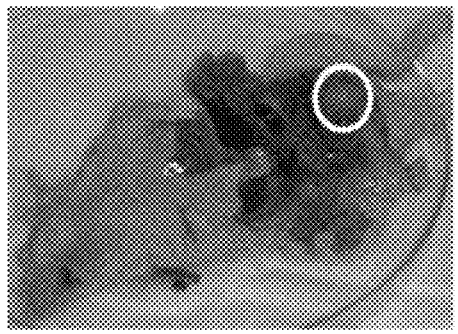
HeyA8 + miR-130b
Tumor weight = 0.3g
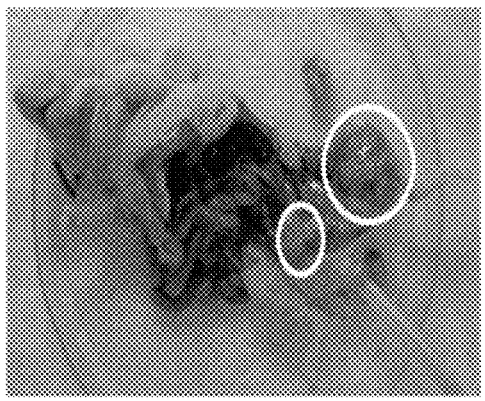
HeyA8 parental:
Tumor weight = 2.0g
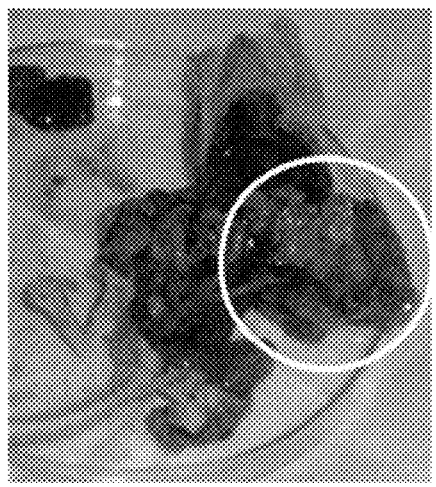
HeyA8 + negative control sequence
Tumor weight = 4.7g
FIG. 3A

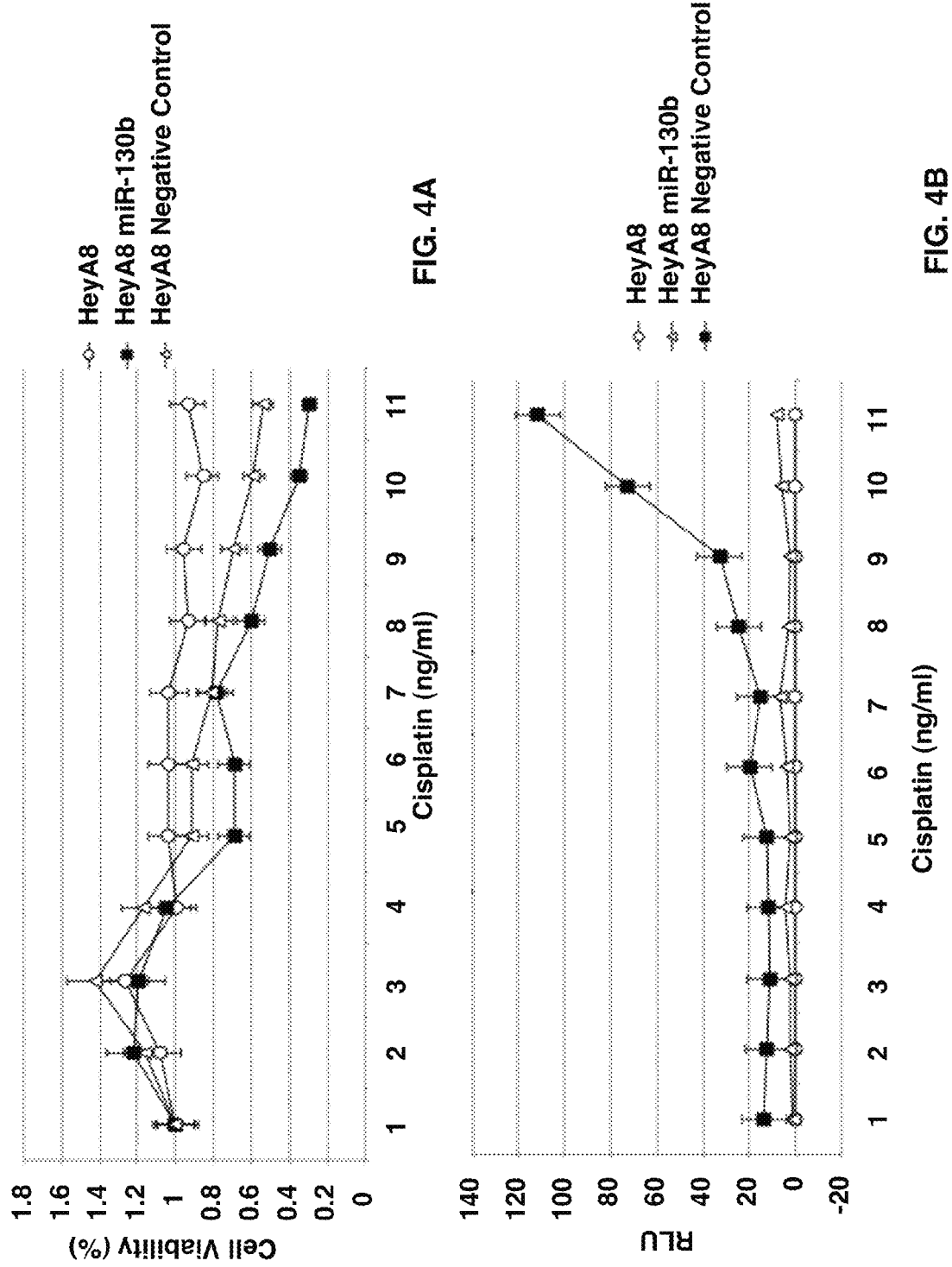

SEQUENCE LISTING

```
<160> NUMBER OF SEQ ID NOS: 28

<210> SEQ ID NO 1
<211> LENGTH: 20
<212> TYPE: DNA
<213> ORGANISM: Artificial Sequence
<220> FEATURE:
<223> OTHER INFORMATION: Forward primer for p53 gene

<400> SEQUENCE: 1
cacatgacgg aggttgtgag                                                   20

<210> SEQ ID NO 2
<211> LENGTH: 20
<212> TYPE: DNA
<213> ORGANISM: Artificial Sequence
<220> FEATURE:
<223> OTHER INFORMATION: Reverse primer for p53 gene

<400> SEQUENCE: 2
acacgcaaat ttccttccac                                                   20

<210> SEQ ID NO 3
<211> LENGTH: 21
<212> TYPE: DNA
<213> ORGANISM: Artificial Sequence
<220> FEATURE:
<223> OTHER INFORMATION: Forward primer for p73 gene

<400> SEQUENCE: 3
gaaggcaata atctctcgca g                                                 21

<210> SEQ ID NO 4
<211> LENGTH: 21
```

```
<212> TYPE: DNA
<213> ORGANISM: Artificial Sequence
<220> FEATURE:
<223> OTHER INFORMATION: Reverse primer for p73 gene

<400> SEQUENCE: 4
atgaagttgt acaggtaggt g                                          21

<210> SEQ ID NO 5
<211> LENGTH: 19
<212> TYPE: DNA
<213> ORGANISM: Artificial Sequence
<220> FEATURE:
<223> OTHER INFORMATION: Forward primer for tap63 gene

<400> SEQUENCE: 5
tgtatccgca tgcaggact                                             19

<210> SEQ ID NO 6
<211> LENGTH: 21
<212> TYPE: DNA
<213> ORGANISM: Artificial Sequence
<220> FEATURE:
<223> OTHER INFORMATION: Reverse primer for tap63 gene

<400> SEQUENCE: 6
ctgtgttata gggactggtg g                                          21

<210> SEQ ID NO 7
<211> LENGTH: 21
<212> TYPE: DNA
<213> ORGANISM: Artificial Sequence
<220> FEATURE:
<223> OTHER INFORMATION: Forward primer for delta-np63 gene

<400> SEQUENCE: 7
gaaaacaatg cccagactca a                                          21

<210> SEQ ID NO 8
<211> LENGTH: 18
<212> TYPE: DNA
<213> ORGANISM: Artificial Sequence
<220> FEATURE:
<223> OTHER INFORMATION: Reverse primer for delta-np63 gene

<400> SEQUENCE: 8
tgcgcgtggt ctgtgtta                                              18

<210> SEQ ID NO 9
<211> LENGTH: 22
<212> TYPE: DNA
<213> ORGANISM: Artificial Sequence
<220> FEATURE:
<223> OTHER INFORMATION: Forward primer for akt1 gene

<400> SEQUENCE: 9
tcctcaagaa ggaagtcatc gt                                         22

<210> SEQ ID NO 10
<211> LENGTH: 22
<212> TYPE: DNA
<213> ORGANISM: Artificial Sequence
<220> FEATURE:
<223> OTHER INFORMATION: Reverse primer for akt1 gene

<400> SEQUENCE: 10
```

```
gtacttcagg gctgtgagga ag                                             22

<210> SEQ ID NO 11
<211> LENGTH: 21
<212> TYPE: DNA
<213> ORGANISM: Artificial Sequence
<220> FEATURE:
<223> OTHER INFORMATION: Forward primer for e2f2 gene

<400> SEQUENCE: 11
aaaaggaagc tggatctgga g                                              21

<210> SEQ ID NO 12
<211> LENGTH: 21
<212> TYPE: DNA
<213> ORGANISM: Artificial Sequence
<220> FEATURE:
<223> OTHER INFORMATION: Reverse primer for e2f2 gene

<400> SEQUENCE: 12
cgaagtgtca taccgagtct t                                              21

<210> SEQ ID NO 13
<211> LENGTH: 21
<212> TYPE: DNA
<213> ORGANISM: Artificial Sequence
<220> FEATURE:
<223> OTHER INFORMATION: Forward primer for pten gene

<400> SEQUENCE: 13
acttgaaggc gtatacagga a                                              21

<210> SEQ ID NO 14
<211> LENGTH: 21
<212> TYPE: DNA
<213> ORGANISM: Artificial Sequence
<220> FEATURE:
<223> OTHER INFORMATION: Reverse primer for pten gene

<400> SEQUENCE: 14
aggatattgt gcaactctgc a                                              21

<210> SEQ ID NO 15
<211> LENGTH: 21
<212> TYPE: DNA
<213> ORGANISM: Artificial Sequence
<220> FEATURE:
<223> OTHER INFORMATION: Forward primer for cdk2 gene

<400> SEQUENCE: 15
cttaagaaaa tccgcctgga c                                              21

<210> SEQ ID NO 16
<211> LENGTH: 21
<212> TYPE: DNA
<213> ORGANISM: Artificial Sequence
<220> FEATURE:
<223> OTHER INFORMATION: Reverse primer for cdk2 gene

<400> SEQUENCE: 16
gcagcttgac aatattagga t                                              21

<210> SEQ ID NO 17
<211> LENGTH: 20
<212> TYPE: DNA
<213> ORGANISM: Artificial Sequence
```

```
<220> FEATURE:
<223> OTHER INFORMATION: Forward primer for cdk6 gene

<400> SEQUENCE: 17
gcccactgaa accataaagg                                              20

<210> SEQ ID NO 18
<211> LENGTH: 21
<212> TYPE: DNA
<213> ORGANISM: Artificial Sequence
<220> FEATURE:
<223> OTHER INFORMATION: Reverse primer for cdk6 gene

<400> SEQUENCE: 18
caccagaatg ttctgtggtt t                                            21

<210> SEQ ID NO 19
<211> LENGTH: 20
<212> TYPE: DNA
<213> ORGANISM: Artificial Sequence
<220> FEATURE:
<223> OTHER INFORMATION: Forward primer for cdkn1a gene

<400> SEQUENCE: 19
aagatgtaga gcgggccttt                                              20

<210> SEQ ID NO 20
<211> LENGTH: 20
<212> TYPE: DNA
<213> ORGANISM: Artificial Sequence
<220> FEATURE:
<223> OTHER INFORMATION: Reverse primer for cdkn1a gene

<400> SEQUENCE: 20
gactctcagg gtcgaaaacg                                              20

<210> SEQ ID NO 21
<211> LENGTH: 26
<212> TYPE: DNA
<213> ORGANISM: Artificial Sequence
<220> FEATURE:
<223> OTHER INFORMATION: Forward primer for mdm2 gene

<400> SEQUENCE: 21
ttggccagta tattatgact aaacga                                       26

<210> SEQ ID NO 22
<211> LENGTH: 22
<212> TYPE: DNA
<213> ORGANISM: Artificial Sequence
<220> FEATURE:
<223> OTHER INFORMATION: Reverse primer for mdm2 gene

<400> SEQUENCE: 22
gctctttcac agagaagctt gg                                           22

<210> SEQ ID NO 23
<211> LENGTH: 21
<212> TYPE: DNA
<213> ORGANISM: Artificial Sequence
<220> FEATURE:
<223> OTHER INFORMATION: Forward primer for rb1 gene

<400> SEQUENCE: 23
tgtctttccc atggattctg a                                            21
```

```
<210> SEQ ID NO 24
<211> LENGTH: 21
<212> TYPE: DNA
<213> ORGANISM: Artificial Sequence
<220> FEATURE:
<223> OTHER INFORMATION: Reverse primer for rb1 gene

<400> SEQUENCE: 24
caagggattc catgattcga t                                            21

<210> SEQ ID NO 25
<211> LENGTH: 19
<212> TYPE: DNA
<213> ORGANISM: Artificial Sequence
<220> FEATURE:
<223> OTHER INFORMATION: Forward primer for 18s gene

<400> SEQUENCE: 25
gatgggcggc ggaaaatag                                               19

<210> SEQ ID NO 26
<211> LENGTH: 21
<212> TYPE: DNA
<213> ORGANISM: Artificial Sequence
<220> FEATURE:
<223> OTHER INFORMATION: Reverse primer for 18s gene

<400> SEQUENCE: 26
gcgtggattc tgcataatgg t                                            21

<210> SEQ ID NO 27
<211> LENGTH: 43
<212> TYPE: RNA
<213> ORGANISM: Artificial Sequence
<220> FEATURE:
<223> OTHER INFORMATION: miR-130b small-interfering RNA

<400> SEQUENCE: 27
rgrgraruru rurcrarurc rurcrururg rururaru rgr                      43

<210> SEQ ID NO 28
<211> LENGTH: 54
<212> TYPE: RNA
<213> ORGANISM: Artificial Sequence
<220> FEATURE:
<223> OTHER INFORMATION: p53 small-interfering RNA

<400> SEQUENCE: 28
rurcrarurc rarurarura rcrarargra rgrarurgra rararurcrc rurc        54
```

MICRORNA-130A,B AS A TUMOR SUPPRESSOR AND SENSITIZING AGENT FOR CHEMOTHERAPY

CROSS-REFERENCE TO RELATED APPLICATIONS

This nonprovisional application claims benefit of provisional application U.S. Ser. No. 61/516,239, filed Mar. 31, 2011, the entirety of which is hereby incorporated by reference.

BACKGROUND OF THE INVENTION

1. Field of the Invention

The present invention relates generally to the fields of microRNA molecular biology and cancer. More specifically, the invention relates to the use of microRNA-130a,b as tumor suppressors able to significantly suppress cell proliferation, increase apoptosis, suppress tumor growth and increase sensitivity of chemotherapeutic drugs.

2. Description of the Related Art

RNA interference refers to the process of sequence-specific post-transcriptional gene silencing in animals mediated by short interfering RNAs (siRNAs) (Fire et al. (1998) Nature 391:806-810). The corresponding process in plants is commonly referred to as post-transcriptional gene silencing (PTGS) or RNA silencing and is also referred to as quelling in fungi. The process of post-transcriptional gene silencing is thought to be an evolutionarily-conserved cellular defense mechanism used to prevent the expression of foreign genes and is commonly shared by diverse flora and phyla (Fire et al. (1999) Trends Genet. 15:358-363). Such protection from foreign gene expression may have evolved in response to the production of double-stranded RNAs (dsRNAs) derived from viral infection or from the random integration of transposon elements into a host genome via a cellular response that specifically destroys homologous single-stranded RNA of viral genomic RNA.

The presence of dsRNA in cells triggers the RNAi response through a mechanism that has yet to be fully characterized. The presence of long dsRNAs in cells stimulates the activity of a ribonuclease III enzyme referred to as dicer. Dicer is involved in the processing of the dsRNA into short pieces of dsRNA known as short interfering RNAs (siRNAs) (Bernstein et al. (2001) Nature 409:363-366). Short interfering RNAs derived from dicer activity are typically about 21 to about 23 nucleotides in length and comprise about 19 base pair duplexes (Elbashir et al. (2001) Genes Dev 15:188-200). Dicer has also been implicated in the excision of 21- and 22-nucleotide small temporal RNAs (stRNAs) from precursor RNA of conserved structure that are implicated in translational control (Hutvagner et al. (2001) Science 293:834-838).

The RNAi response also features an endonuclease complex, commonly referred to as an RNA-induced silencing complex (RISC), which mediates cleavage of single-stranded RNA having sequence complementarity to the antisense strand of the siRNA duplex. Cleavage of the target RNA takes place in the middle of the region complementary to the antisense strand of the siRNA duplex (Elbashir et al. (2001) Genes Dev 15:188-200). In addition, RNA interference can also involve small RNA (e.g., microRNA, or miRNA) mediated gene silencing, presumably through cellular mechanisms that regulate chromatin structure and thereby prevent transcription of target gene sequences (see, e.g., Allshire, Science 297:1818-1819 2002; Volpe et al. (2002) Science 297:1833-1837; Jenuwein (2002) Science 297:2215-2218; Hall et al. (2002) Science 297:2232-2237).

As such, miRNA molecules of the invention can be used to mediate gene silencing via interaction with RNA transcripts or alternately by interaction with particular gene sequences, wherein such interaction results in gene silencing either at the transcriptional or post-transcriptional level. RNAi has been studied in a variety of systems. Fire et al. ((1998) Nature 391:806-811) were the first to observe RNAi in C. elegans. Wianny and Goetz ((1999) Nature Cell Biol 2:70) describe RNAi mediated by dsRNA in mouse embryos. Hammond et al. ((2000) Nature 404:293-296) describe RNAi in Drosophila cells transfected with dsRNA. Elbashir et al. ((2001) Nature 411:494-498) describe RNAi induced by introduction of duplexes of synthetic 21-nucleotide RNAs in cultured mammalian cells including human embryonic kidney and HeLa cells.

Small RNAs play an important role in controlling gene expression. Regulation of many developmental processes is controlled by small RNAs. It is now possible to engineer changes in gene expression of plant genes by using transgenic constructs which produce small RNAs in the plant. Small RNAs appear to function by base-pairing to complementary RNA or DNA target sequences. When bound to RNA, small RNAs trigger either RNA cleavage or translational inhibition of the target sequence. When bound to DNA target sequences, it is thought that small RNAs can mediate DNA methylation of the target sequence. The consequence of these events, regardless of the specific mechanism, is that gene expression is inhibited. It is thought that sequence complementarity between small RNAs and their RNA targets helps to determine which mechanism, RNA cleavage or translational inhibition, is employed. It is believed that siRNAs, which are perfectly complementary with their targets, work by RNA cleavage. Some miRNAs have perfect or near-perfect complementarity with their targets, and RNA cleavage has been demonstrated for at least a few of these miRNAs. Other miRNAs have several mismatches with their targets, and apparently inhibit their targets at the translational level.

Without being held to a particular theory on the mechanism of action, a general rule is emerging that perfect or near-perfect complementarity favors RNA cleavage, especially within the first ten nucleotides (counting from the 5' end of the miRNA), whereas translational inhibition is favored when the miRNA/target duplex contains many mismatches. The apparent exception to this is microRNA-172 (miR172) in plants. One of the targets of miR172 is APETALA2 (AP2), and although miR172 shares near-perfect complementarity with AP2 it appears to cause translational inhibition of AP2 rather than RNA cleavage. MicroRNAs (miRNAs) are noncoding RNAs of about 19 to about 24 nucleotides (nt) in length that have been identified in both animals and plants (Lagos-Quintana et al. (2001) Science 294:853-858, Lagos-Quintana et al. (2002) Curr Biol 12:735-739; Lau et al. (2002) Science 294:858-862; Lee and Ambros (2001) Science 294:862-864; Llave et al. (2002) Plant Cell 14:1605-1619; Mourelatos et al. (2002) Genes Dev 16:720-728; Park et al. (2002) Curr Biol 12:1484-1495; Reinhart et al. (2002) Genes Dev 16:1616-1626). They are processed from longer precursor transcripts that range in size from approximately 70 to 200 nt, and these precursor transcripts have the ability to form stable hairpin structures. In animals, the enzyme involved in processing miRNA precursors is called Dicer, an RNAse III-like protein (Grishok et al. (2001) Cell 106:23-34; Hutvagner et al. (2001) Science 293:834-838; Ketting et al. (2001) Genes Dev 15:2654-2659). Plants also have a Dicer-like enzyme, DCL1 (previously named CARPEL FACTORY/SHORT INTEGU- MENTS1/SUSPENSOR1), and recent evidence indicates that it, like Dicer, is involved in processing the hairpin precursors to generate mature miRNAs (Park et al. (2002) Curr Biol 12:1484-1495; Reinhart et al. (2002) Genes Dev 16:1616-1626).

Furthermore, it is becoming clear from recent work that at least some miRNA hairpin precursors originate as longer polyadenylated transcripts, and several different miRNAs and associated hairpins can be present in a single transcript (Lagos-Quintana et al. (2001) Science 294:853-858; Lee et al. (2002) EMBO J. 21:4663-4670). Recent work has also examined the selection of the miRNA strand from the dsRNA product arising from processing of the hairpin by DICER (Schwartz et al. (2003) Cell 115:199-208). It appears that the stability (i.e. G:C vs. A:U content, and/or mismatches) of the two ends of the processed dsRNA affects the strand selection, with the low stability end being easier to unwind by a helicase activity. The 5' end strand at the low stability end is incorporated into the RISC complex, while the other strand is degraded. In animals, there is direct evidence indicating a role for specific miRNAs in development. The lin-4 and let-7 miRNAs in *C. elegans* have been found to control temporal development, based on the phenotypes generated when the genes producing the lin-4 and let-7 miRNAs are mutated (Lee et al. (1993) Cell 75:843-854; Reinhart et al. (2000) Nature 403-901-906).

In addition, both miRNAs display a temporal expression pattern consistent with their roles in developmental timing. Other animal miRNAs display developmentally regulated patterns of expression, both temporal and tissue-specific (Lagos-Quintana et al. (2001) Science 294:853-853, Lagos-Quintana et al. (2002) Curr Biol 12:735-739; Lau et al. (2001) Science 294:858-862; Lee and Ambros (2001) Science 294: 862-864), leading to the hypothesis that miRNAs may, in many cases, be involved in the regulation of important developmental processes. Likewise, in plants, the differential expression patterns of many miRNAs suggests a role in development (Llave et al. (2002) Plant Cell 14:1605-1619; Park et al. (2002) Curr Biol 12:1484-1495; Reinhart et al. (2002) Genes Dev 16:1616-1626), which has now been shown (e.g., Guo et al. (2005) Plant Cell 17:1376-1386).

MicroRNAs appear to regulate target genes by binding to complementary sequences located in the transcripts produced by these genes. In the case of lin-4 and let-7, the target sites are located in the 3' UTRs of the target mRNAs (Lee et al. (1993) Cell 75:843-854; Wightman et al. (1993) Cell 75:855-862; Reinhart et al. (2000) Nature 403:901-906; Slack et al. (2000) Mol Cell 5:659-669), and there are several mismatches between the lin-4 and let-7 miRNAs and their target sites. Binding of the lin-4 or let-7 miRNA appears to cause downregulation of steady-state levels of the protein encoded by the target mRNA without affecting the transcript itself (Olsen and Ambros (1999) Dev Biol 216:671-680).

On the other hand, recent evidence suggests that miRNAs can, in some cases, cause specific RNA cleavage of the target transcript within the target site, and this cleavage step appears to require 100% complementarity between the miRNA and the target transcript (Hutvagner and Zamore (2002) Science 297:2056-2060; Llave et al. (2002) Plant Cell 14:1605-1619), especially within the first ten nucleotides (counting from the 5' end of the miRNA). It seems likely that miRNAs can enter at least two pathways of target gene regulation. Protein downregulation when target complementarity is <100%, and RNA cleavage when target complementarity is 100%. MicroRNAs entering the RNA cleavage pathway are analogous to the 21-25 nt short interfering RNAs (siRNAs) generated during RNA interference (RNAi) in animals and posttranscriptional gene silencing (PTGS) in plants (Hamilton and Baulcombe (1999) Science 286:950-952; Hammond et al., (2000) Nature 404:293-296; Zamore et al., (2000) Cell 31:25-33; Elbashir et al., (2001) Nature 411:494-498), and likely are incorporated into an RNA-induced silencing complex (RISC) that is similar or identical to that seen for RNAi.

Identifying the targets of miRNAs with bioinformatics has not been successful in animals, and this is probably due to the fact that animal miRNAs have a low degree of complementarity with their targets. On the other hand, bioinformatic approaches have been successfully used to predict targets for plant miRNAs (Llave et al. (2002) Plant Cell 14:1605-1619; Park et al. (2002) Curr Biol 12:1484-1495; Rhoades et al. (2002) Cell 110:513-520), and thus it appears that plant miRNAs have higher overall complementarity with their putative targets than do animal miRNAs. Most of these predicted target transcripts of plant miRNAs encode members of transcription factor families implicated in plant developmental patterning or cell differentiation. Nonetheless, biological function has not been directly demonstrated for any plant miRNA. Although Llave et al. ((2002) Science 297:2053-2056) have shown that a transcript for a SCARECROW-like transcription factor is a target of the Arabidopsis miRNA mir171, these studies were performed in a heterologous species and no plant phenotype associated with mir171 was reported.

General categories of sequences of interest for the invention described include, for example, those genes involved in regulating oncogenic processes that are responsible for the initiation, progression or maintenance of increased cell proliferation and/or decreased cell death that are direct or indirect targets of tumor suppressor microRNAs. Target sequences further include coding regions and non-coding regions such as promoters, enhancers, terminators, introns and the like, which may be modified in order to alter the expression of a gene of interest. For example, an intron sequence can be added to the 5' region to increase the amount of mature message that accumulates (see for example Buchman and Berg (1988) Mol Cell Biol 8:4395-4405); and Callis et al. (1987) Genes Dev 1:1183-1200). This current invention is about microRNAs are small-22 nucleotide non-coding RNAs that can bind protein coding mRNAs through complimentary base pairing to mediate mRNA decay or translational repression. Because a single microRNA can bind and silence hundreds of genes across diverse signaling pathways they can be developed as powerful therapeutic agents to silence entire disease networks.

The prior art is deficient in the use of the microRNA-130a, microRNA-130b, microRNA-130c to, inter alia, significantly enhance sensitivity to chemotherapeutic drug as well as provide an alternative or complement to small molecule inhibitor treatment for ovarian and other cancers.

SUMMARY OF THE INVENTION

The present invention is directed to the use of the microRNA-130a and microRNA-130b microRNA family to, inter alia, significantly enhance sensitivity to chemotherapeutic drug as well as provide an alternative or complement to small molecule inhibitor treatment for ovarian and other cancers when presented in the form of pri-miRNA, pre-miRNA, mature miRNA or fragments of variants thereof that retain the biological activity of the mature miRNA and DNA encoding a pri-miRNA, pre-miRNA, mature miRNA, fragments or variants thereof, or regulatory elements of the miRNA.

Thus, in one embodiment of the present invention, there is provided a method of providing a prognosis for ovarian cancer in a subject, comprising the steps of: obtaining a biological sample from said subject; and testing said biological sample to determine whether or not microRNA-130 (miR-130) is under-expressed in said sample, relative to the expression of microRNA-130 in a control sample, whereby the under-expression of microRNA-130 in the biological sample indicates that a tumor in the subject is resistant to a chemotherapy.

In another embodiment of the present invention, there is provided a method of improving a therapeutic response to a cancer treatment in a subject, the method comprising administering an effective amount of a microRNA-130 or an agent that mimic the effects or enhance expression of microRNA-130. Representative microRNA-130 compounds include microRNA-130a and microRNA-130b. Representative agents that mimic the effects or enhance expression of microRNA-130 include but are not limited to double-stranded miRNA 130 mimics and oligonucleotide based pre-microRNA-130 drugs.

Representative cancers include but are not limited to lung cancer, pancreatic cancer, skin cancer, hematological neoplasms, breast cancer, brain cancer, colon cancer, follicular lymphoma, bladder cancer, cervical cancer, endometrial cancer, esophageal cancer, gastric cancer, head and neck cancer, multiple myeloma, liver cancer, lymphomas, oral cancer, osteosarcomas, ovarian cancer, uterine leiomyosarcoma, uterine leiomyomas, endometriomas, endometriosis, uterine papillary serous carcinomas, prostate cancer, testicular cancer and thyroid cancer. In a preferred embodiment, the cancer is epithelial ovarian cancer. Representative therapeutic responses include but are not limited to treating with radiation, carboplatin, cisplatin, paclitaxel, an alkylating agent, an antimetabolite, an antitumor antibiotic, and a DNA topoisomerase inhibitor.

In yet another embodiment of the present invention, there is provided a kit for determining a chemotherapy response in a patient with a cancer, said kit comprising: a) a oligonucleotide complementary to microRNA-130; and b) optionally, reagents for the formation of the hybridization between said oligonucleotide and said microRNA-130. In one aspect, the microRNA-130 may be detectably labeled. A person with ordinary skill in this art would recognize that, in this kit, the microRNA-130 could attached to a solid surface. For example, the microRNA-130 could be a member or component of a nucleic acid array. A representative example of a nucleic acid array is a micro-array.

In yet another embodiment of the present invention, there is provided a pharmaceutical composition for improving a tumor response to chemotherapy, said composition comprising an effective amount of microRNA-130a or microRNA-130b or an agent that enhances the expression of microRNA-130a or microRNA-130b or mimics the actions of microRNA-130a or microRNA-130b. The pharmaceutical composition could be delivered on a nanoliposomal vector, gold or other nanoparticle carriers or viral vectors with and without genes such as p53.

In yet another embodiment of the present invention, there is provided a method of treating a cancer in a subject in need of such treatment comprising the step of administering an effective amount of a microRNA-130a or microRNA-130b or an agent that enhances the expression of microRNA-130a or microRNA-130b or mimics the actions of microRNA-130a or microRNA-130b. In this method, the microRNA-130 may be microRNA-130a or microRNA-130b. Representative examples of an agent that enhances the expression of microRNA-130 or mimics the actions of microRNA-130 include double-stranded miRNA mimics, and oligonucleotide based pre-microRNA-130 drugs. The microRNA-130 mimics and/or drugs can be delivered on liposomal, gold or other nanoparticle carriers, or nanoliposomal vectors into human patients.

Representative examples of cancer which may be treated using this method include but are not limited to lung cancer, pancreatic cancer, skin cancer, hematological neoplasms, breast cancer, brain cancer, colon cancer, follicular lymphoma, bladder cancer, cervical cancer, endometrial cancer, esophageal cancer, gastric cancer, head and neck cancer, multiple myeloma, liver cancer, lymphomas, oral cancer, osteosarcomas, ovarian cancer, uterine leiomyosarcoma, uterine leiomyomas, endometriomas, endometriosis, uterine papillary serous carcinomas, prostate cancer, testicular cancer and thyroid cancer. In a preferred aspect, the cancer is epithelial ovarian cancer. In a further embodiment, this method may further comprise treating the subject with radiation, carboplatin, cisplatin, paclitaxel, an alkylating agent, an antimetabolite, an antitumor antibiotic and a DNA topoisomerase inhibitor. A person having ordinary skill in this art would readily recognize that the microRNA-130 or agent that enhances the expression of microRNA-130 or mimics the actions of microRNA-130a,b may be administered as a nucleic acid construct encoding an artificial miRNA presented as a double-stranded RNA, a precursor hairpin, a primary miRNA in single straded RNA form, encoded in a DNA vector delivered in a suitable pharmaceutical carrier. Representative examples of a pharmaceutical carrier which may be used in this method include but are not limited to a virus, a liposome, a polymer and a nanoparticle carrier. The microRNA-130 may be administered as a nanoparticle, a liposome, a vector or a polymer. Representative examples of vector which may be used in this method include but are not limited to a plasmid, a cosmid, a phagemid and a virus.

Other and further aspects, features, benefits, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions and certain embodiments of the invention briefly summarized above are illustrated in the appended drawings. These drawings form a part of the specification. It is to be noted, however, that the appended drawings illustrate preferred embodiments of the invention and therefore are not to be considered limiting in their scope.

FIGS. 1A and 1C show the impact of miR-130b on cell proliferation as measured by the standard MTT assay. FIGS. 1B and 1D show the impact of miR-130b on apoptosis as measured by caspase activity. In each case miR-130b is shown in red and compared with a scrambled control (blue, grey or green) and the parental strain (black).

FIGS. 2A and 2C show the impact of miR-130b on cell proliferation as measured by the standard MTT assay. FIGS. 2B and 2D show the impact of miR-130b on apoptosis as measured by caspase activity. In each case miR-130b is shown in red and compared with a scrambled control (blue, grey or green) and the parental strain (black). From data shown it is clear that the CDKN2A-deficient cell lines do not show a major impact of miR-130b on cell proliferation or apoptosis.

FIGS. 3A-3C. Impact of miR-130b on in vivo tumor growth and burden. This figure shows the summary of in vivo work performed. Nude mice were injected ~2.0×106 cells with overexpression of either miR-130b or a scramble control. Mice were imaged weekly using the Xenogen IVIS system. 10 minutes after intraperitoneal injection of D-luciferin [40 mg/kg body weight]. After 6 weeks, animals were sacrificed (FIG. 3A) and weights of tumors (FIG. 3C) were assessed and compared. Mice were subjected to in vivo bioluminescence imaging (FIG. 3B) using an IVIS Spectrum, and the results were quantified via Living Image software.

FIGS. 4A-4B: Impact of miR-130b on Cisplatin Dose-Response Curves. Cisplatin treated HeyA8 cells with either miR-130b or a negative control proliferation and apoptosis assays were measured 72 hours following treatment with cisplatin at the indicated concentrations. The assays were measured using MTS (FIG. 4A) and Caspase-Glo 3/7 (FIG. 4B) assays. The $IC_{50}$ (concentration needed to reach 50% viability) values are shown beside the MTA graph.

DESCRIPTION OF THE PREFERRED EMBODIMENTS

Figure 1A:
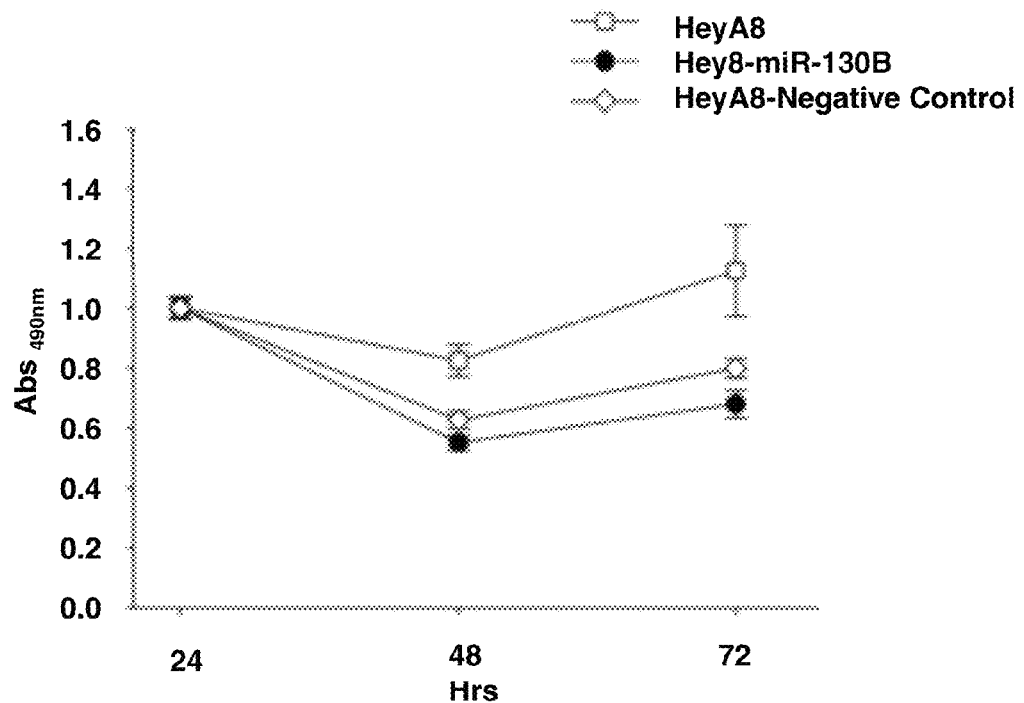
FIGS. 1A-1D: Impact of miR-130b depends on the p53 and CDKN2A phenotype. The p53mut-loss of function cell lines OVCAR8 (FIGS. 1A-1B) and p53-wild type HEYA8 (FIGS. 1C-1D) were employed to examine the role of p53 in miR-130b function.

As used herein, the term "a" or "an", when used in conjunction with the term "comprising" in the claims and/or the specification, may refer to "one," but it is also consistent with the meaning of "one or more," "at least one," and "one or more than one." Some embodiments of the invention may consist of or consist essentially of one or more elements, method steps, and/or methods of the invention. It is contemplated that any method or composition described herein can be implemented with respect to any other method or composition described herein.

As used herein, the term "or" in the claims refers to "and/or" unless explicitly indicated to refer to alternatives only or the alternatives are mutually exclusive, although the disclosure supports a definition that refers to only alternatives and "and/or."

The present invention relates to the design, synthesis, construction, composition, characterization and use of a therapeutic microRNAs and methods useful in treating cancer using such microRNAs. More specifically, the invention discloses that artificial microRNA-130a,b are potent tumor suppressors able to significantly suppress cell proliferation, increase apoptosis, suppress tumor growth and increase sensitivity of chemotherapeutic drugs when presented in the form of pri-miRNA, pre-miRNA, mature miRNA or fragments of variants thereof that retain the biological activity of the mature miRNA and DNA encoding a pri-miRNA, pre-miRNA, mature miRNA, fragments or variants thereof, or regulatory elements of the miRNA.

One preferred embodiment of the invention discloses the use of a nucleic acid construct encoding an artificial miRNA presented as a double-stranded RNA or precursor a hairpin or a primary miRNA in the single straded RNA form or encoded in a DNA vector delivered in a suitable pharmaceutical carrier, to be used for inhibiting the expression of all oncogenes and regulators of oncogenes containing a miR-130a,b complementary site (LCS). The pharmaceutical carrier includes, but is not limited to, a virus, a liposome, or a polymer, and any combination thereof.

Another preferred embodiment of the present invention discloses the composition, methods and use of a nucleic acid construct encoding an artificial miRNA presented as a double-stranded RNA or precursor a hairpin or a primary miRNA in the single stranded RNA form or encoded in a DNA vector delivered in a suitable pharmaceutical carrier, to be used for inhibiting the expression of all oncogenes and regulators of oncogenes containing a miR-130a,b complementary site (LCS), wherein the miR-130a,b is delivered in multiple ways, to include but not limited to, as a mature miRNA by itself, or as a gene is encoded by a nucleic acid, or as a precursor hairpin by itself or conjugated to nanoparticles of metal or liposomal origin, or conjugated to nanoparticles of metal or liposomal origin, or as a primary miRNA by itself or conjugated to nanoparticles of metal or liposomal origin or delivered on a virus, or as a liposome, or as a polymer, or as a gene that is encoded by a nucleic acid and such nucleic acid is located on a vector, or as a gene is encoded by a nucleic acid, or as a precursor hairpin by itself or conjugated to nanoparticles of metal or liposomal origin.

Another preferred embodiment of the present invention discloses that such nucleic acid is located on a vector selected from the group consisting of a plasmid, cosmid, phagemid, virus, and other vehicles derived from viral or bacterial sources, or is located on a vector that may further comprises one or more in vivo expression elements selected from the group consisting of a promoter, enhancer, and combinations thereof.

Another preferred embodiment of the present invention relates to the use of miR-130a,b where the miRNA is administered to, or expression is increased in the cells of, a patient for treatment or prevention of cancer, including but not limited to lung cancer, pancreatic cancer, skin cancer, hematological neoplasms, breast cancer, brain cancer, colon cancer, follicular lymphoma, bladder cancer, cervical cancer, endometrial cancer, esophageal cancer, gastric cancer, head and neck cancer, multiple myeloma, liver cancer, lymphomas, oral cancer, osteosarcomas, ovarian cancer, prostate cancer, testicular cancer, and/or thyroid cancer.

Another preferred embodiment of the present invention relates to the use of miR-130a,b where miRNA is administered to, or expression is increased in the cells of, a patient for treatment or prevention of cancer and wherein the patient is undergoing one or more cancer therapies selected from the group consisting of surgery, chemotherapy, radiotherapy, thermotherapy, immunotherapy, hormone therapy and laser therapy.

Another embodiment of the present invention discloses a method for determining the sensitivity of a cancer to a miR-130a,b miRNA delivered on a suitable pharmaceutical carrier to bind to an mRNA encoded by an oncogene containing one or several miR-130a,b complementary site (LCS) in a cancerous or transformed cell or an organism with a cancerous or transformed cell; and determining if the cancerous or transformed cell growth or viability is inhibited or if expression of the oncogene is inhibited.

A preferred embodiment of the present invention discloses that miR-130b inhibits proliferation in p53-deficient ovarian cancer cell lines (OVCAR8) as well as p53-wild type cells (HEYA8) as shown in FIGS. 1A-1D. In addition, apoptosis was not affected in p53-deficient ovarian cancer cell lines (OVCAR8). The rate of apoptosis was increased in p53-wild type cells (HEYA8) cells (FIGS. 1A-1D). These results suggest miR-130b is capable of retarding tumor growth and/or promoting tumor cells to undergo cellular apoptosis. The implication of such finding is that miR-130b can increase the overall survival of ovarian cancer patients including those with a poor prognosis due to a loss of treatment response most commonly caused by a loss of p53.

Another embodiment of the present invention discloses that miR-130b is able to suppress the growth of tumors and reduce tumor burden in mice injected with the HEYA8 parental strain, HEYA8 stably transfected with a lentiviral vector expressing a scrambled control sequence, and HEYA8 stably transfected with a lentiviral vector expressing miR-130b hairpin, as illustrated in FIGS. 2A-2D and 3A-3C. (ROIs) were established for individual tumors using Living Image® Software v.2.5, and luminescent signal for those tumors was measured in photons/second/cm2/steradian (p/s). The data suggests that miR-130b is able to significantly reduce tumor burden in this xenograft mouse model.

Another embodiment of the present invention discloses that miR-130b increases the sensitivity of HeyA8 ovarian cancer cells to the chemotherapeutic agent cisplatin. As illustrated in FIGS. 4A-4B, HeyA8 with miR-130b shows a decrease in proliferation (MTS) compared to the parental and miR scrambled controls suggesting increased sensitivity to cisplatin in the presence of miR-130b. HeyA8 with miR-130b has a significant induction of caspase activation correlating with an increase in apoptosis compared to the parental and miR scramble controls. From these data one may conclude that miR-130b and its family member miR-130a could significantly increase the sensitivity of tumors to chemotherapy in ovarian and other cancers. The implications of such findings is that patients that are able to respond to current doses of chemotherapy can be treated with much lower doses of chemotherapy when presented with miR-130b,a. Also, patients that do not respond to chemotherapy, or patients that respond but relapse, can be successfully treated with regular doses of chemotherapy+miR-130b or miR-130a. In addition, since miR-130b is highly effective at suppressing the proliferation and increasing cell death of p53-wild type ovarian cancer cells it is likely to be effective in treating low grade tumors as well.

While the invention described here specifically relates to the design and construction of a novel therapeutic agents such as nucleic acids (microRNAs) to treat cancer, one of ordinary skill in the art, with the benefit of this disclosure, would be able to extend the proposed microRNAs to be used in many kinds of cancer treatments, and would recognize the extension of the approach to other treatment protocols.

The following examples are given for the purpose of illustrating various embodiments of the invention and are not meant to limit the present invention in any fashion. One skilled in the art will appreciate readily that the present invention is well adapted to carry out the objects and obtain the ends and advantages mentioned, as well as those objects, ends and advantages inherent herein. Changes therein and other uses which are encompassed within the spirit of the invention as defined by the scope of the claims will occur to those skilled in the art.

EXAMPLE 1

Cell Lines and Growth Conditions

Ovarian cancer cell lines HeyA8, SKOV3ip1, OVCAR8, and OV-90 were obtained from the ATCC (Bethesda, Md.). HeyA8, SKOV3ip1, OVCAR8 cell lines were maintained in RPMI 1640 with 10% Fetal Bovine Serum (FBS) and 1% Pen/Strep. OV-90 and HEK293T were maintained in a 1:1 mix of Medium199/MCDB-105 (Sigma) with 15% FBS and DMEM with 10% FBS respectively each containing 1% pen/strep. All cells were maintained at 37° C. in 5% $CO_2$.

EXAMPLE 2 miRNA Over Expression by Transient Transfection $(2.5 \times 10^5)$ cells were seeded per well in 6 well plates 24 hours before transfection. MicroRNA mimics and scrambled miRNA control (SCR) (Ambion) were transfected according to the manufacturer's instructions using 25 nM mimic or control and 4 µL of Lipofectamine 2000 (Invitrogen) per transfection. After 24 hours, the transfection medium was removed and cells were washed with DPBS.

EXAMPLE 3

Lentiviral Packaging and Delivery for miRNA Over Expression

HEK293T cells were used to package viral particles containing either pmiR-130b or pmiR-negative control and pLent-luc-neo plasmid (Genecopeia). Packaging was obtained from Dr. Robert Schwartz's lab (University of Houston). $2.5 \times 10^5$ cells were reverse transfected with 400 uL of active virus particles in the presence of polybrene. After 24 hours, the medium was removed and the cells were washed with DPBS before replacing growth medium.

EXAMPLE 4

Proliferation Assays

Cell viability was assessed using Promega's CellTiter 96AQueous non-radioactive cell proliferation assay. Briefly, the cells were seeded at 1,000 cells/well in a 96-well microtiter plate 24 hours following transfection at a final volume of 100 µL. Measurements were taken at 48, 72, and 96 hour time points following the addition of 20 µL MTS reagent to each well and then incubated for 90 minutes at 37° C. in 5% $CO_2$. Absorbance of each well was read at 490 nm using a microplate reader from BioTek. Each sample was normalized to the 48 hour time point.

EXAMPLE 5

Activation of Apoptosis Assays

In parallel with the proliferation assays, apoptosis was assessed using the Caspase 3/7 Glo assay from Promega.

Briefly, the cells were seeded at 1,000 cells/well in a 96-well microtiter plate 24 hours following transfection with microRNA mimics and controls at a final volume of 100 µL. Measurements were taken at 48, 72, and 96 hour time points following the addition of 100 µL to each well and then incubated for 90 minutes at room temperature shielded from light. The luminescence from each well was measured at using a microplate reader from BioTek. Each sample was normalized to the 48-hour time point.

EXAMPLE 6

Total RNA Isolation 96 hours after transfection, cells were washed with DPBS, harvested and centrifuged at 5,000 rpm for 5 minutes, and then snap frozen with liquid nitrogen. All RNA was isolated using the Mirvana kit from Ambion following the manufacturer's instructions and quantified at 260 nm with the Nanodrop spectrophotometer.

EXAMPLE 7

Reverse Transcription and Quantitative PCR

For gene expression analysis of target genes, 75 ng of total RNA from each sample was reverse transcribed using the qScript cDNA Super mix from Quanta Biosciences (95048). All RT-qPCR was carried out with the Veriti OneStep from Applied Biosystems. All qPCR experiments used the microCt method and Power SYBR Green Master Mix (Applied Biosystems). 18S was used as the endogenous control for all targets. The primer sets for 18s, p53, p63, p73, CDK2, CDK6, Rb1, PTEN, p21, MDM2, E2F2, are given in Table 1.

TABLE 1

| Gene | Forward Primer 5'->3' | Reverse Primer 5'->3' |
| --- | --- | --- |
| P53 | CACATGACGGAGGTTGTGAG (SEQ ID NO: 1) | ACACGCAAATTTCCTTCCAC (SEQ ID NO: 2) |
| P73 | GAAGGCAATAATCTCTCGCAG (SEQ ID NO: 3) | ATGAAGTTGTACAGGTAGGTG (SEQ ID NO: 4) |
| TAp63 | TGTATCCGCATGCAGGACT (SEQ ID NO: 5) | CTGTGTTATAGGGACTGGTGG (SEQ ID NO: 6) |
| δNp63 | GAAAACAATGCCCAGACTCAA (SEQ ID NO: 7) | TGCGCGTGGTCTGTGTTA (SEQ ID NO: 8) |
| AKT1 | TCCTCAAGAAGGAAGTCATCGT (SEQ ID NO: 9) | GTACTTCAGGGCTGTGAGGAAG (SEQ ID NO: 10) |
| E2F2 | AAAAGGAAGCTGGATCTGGAG (SEQ ID NO: 11) | CGAAGTGTCATACCGAGTCTT (SEQ ID NO: 122) |
| PTEN | ACTTGAAGGCGTATACAGGAA (SEQ ID NO: 13) | AGGATATTGTGCAACTCTGCA (SEQ ID NO: 14) |
| CDK2 | CTTAAGAAAATCCGCCTGGAC (SEQ ID NO: 15) | GCAGCTTGACAATATTAGGAT (SEQ ID NO: 16) |
| CDK6 | GCCCACTGAAACCATAAAGG (SEQ ID NO: 17) | CACCAGAATGTTCTGTGGTTT (SEQ ID NO: 18) |
| CDKN1A (p21) | AAGATGTAGAGCGGGCCTTT (SEQ ID NO: 19) | GACTCTCAGGGTCGAAAACG (SEQ ID NO: 20) |
| MDM2 | TTGGCCAGTATATTATGACTAAACGA (SEQ ID NO: 21) | GCTCTTTCACAGAGAAGCTTGG (SEQ ID NO: 22) |
| RB1 | TGTCTTTCCCATGGATTCTGA (SEQ ID NO: 23) | CAAGGGATTCCATGATTCGAT (SEQ ID NO: 24) |
| 18s | GATGGGCGGCGGAAAATAG (SEQ ID NO: 25) | GCGTGGATTCTGCATAATGGT (SEQ ID NO: 26) |

Table 1. Primer sequences for ciRT-PCR. This table lists the sequences of the complete set of primer pairs used for qRT-PCR using SYBR green. Primers were designed using Primer3 and verified in silico with UCSC Blat to the human genome (hg19). Each set was also verified for amplicon size and off target amplification using PCR and the PCR products analyzed by gel electrophoresis in a 2% agarose gel.

EXAMPLE 8 dIRT-PCR for MicroRNA Expression 10 ng of total RNA was reverse transcribed using the specific stem-loop RT primers with the TaqMan microRNA reverse transcription kit (Applied Biosystems) according to the manufacturer's instruction. 2×qPCR Taqman Master Mix (with no amperase, ABI) was combined with cDNA and analyzed using the µCt method on the Veriti OneStep from Applied Biosystems. All PCR reactions were performed in triplicate and miRNA expression levels were normalized using RNU6B.

EXAMPLE 9

Generation of HeyA8 Cells with Luciferase

HeyA8 cell were transduced with pLenti-PGK-V5luc-Neo packaged in active lenti-particles for 24 hours and then normal growth medium was replaced. Selection medium with G418, was added 48 hours after initial transduction. These cells lines were made for in vivo studies and were co-transduced again with pmiR-130b or SCR.

EXAMPLE 10

In Vivo Xenografts

CrTac: NCr-foxnlnu (Nude) mice were injected with ~2.0× $10^6$ HeyA8 cells over-expressing lentivirally delivered pmiR-130b or a pmiR-negative control. Mice were anesthetized and in vivo imaged weekly using the Xenogen IVIS system after intraperitoneal injection of D-luciferin [40 mg/kg body weight]. After 4 weeks, all animals were sacrificed and individual and total weights of tumor were assessed and compared. All results were quantified using Living Image software.

EXAMPLE 11

Cisplatin Treatment

To assess the impact of miR-130b on cisplatin treatment, HEYA8 cells transfected with pmiR-130b, Negative control or nothing at a density of 2500 cells/well. Cells were treated with cisplatin across a range of concentrations from 0-10 µg/mL. After 72 hours, cells were assayed for growth and apoptosis activity using MTS and Caspase 3/7 assays from Promega as described before. Each sample was normalized to the parental non treated sample.

EXAMPLE 12 siRNA Treatments

To determine the role of p53 in miR-130b gene regulation the HEYA and OVCAR8 cell lines were co-transfected with miR-130b and p53 siRNA (IDT_HSC.RNAI.N000546.12.2, 5'-rGrGrA rUrUrU rCrArU rCrUrC rUrUrG rUrArU rArU-rGr A-3', SEQ ID NO: 27), 5'-rUrCrA rUrCrA rUrArU rAr-CrA rArGrA rGrArU rGrArA rArUrC rCrUrC-3', SEQ ID NO: 28) 72 hrs post-transfection gene expression was assayed by Q-PCR as described before.

EXAMPLE 13 miR-130b Acts as a Tumor Suppressor of Ovarian Cancer In Vitro

To examine the functional impact of miR-130b on cell cycle arrest and apoptosis, mimics for miR-130b were delivered into a series of ovarian cancer cell lines with distinct p53 and CDKN2A genetic backgrounds. To explore the impact of miR-130b on ovarian cancer with respect to key cell cycle regulators the high-grade serous ovarian cancer cell lines HeyA8 (p53$^+$ CDKN2A$^+$), OVCAR8 (p53$^-$ CDKN2A$^+$), and SKOV3ip1 (CDKN2A$^-$ and p53$^-$) and Grade IIIc ovarian cancer cell line OV-90 (CDKN2A$^{mut}$ and p53$^{mut}$) were utilized. Following transfection with precursors for miR-130b or a negative miRNA control (NC), ovarian cancer cells were serially monitored at 24, 48 and 72 hours for proliferation and apoptosis using the MTS and Caspase 3/7 assays, respectively. miR-130b and a NC were delivered using either miRNA mimics (Ambion) or lentiviral vectors (Genecopeia).

Figure 1B:
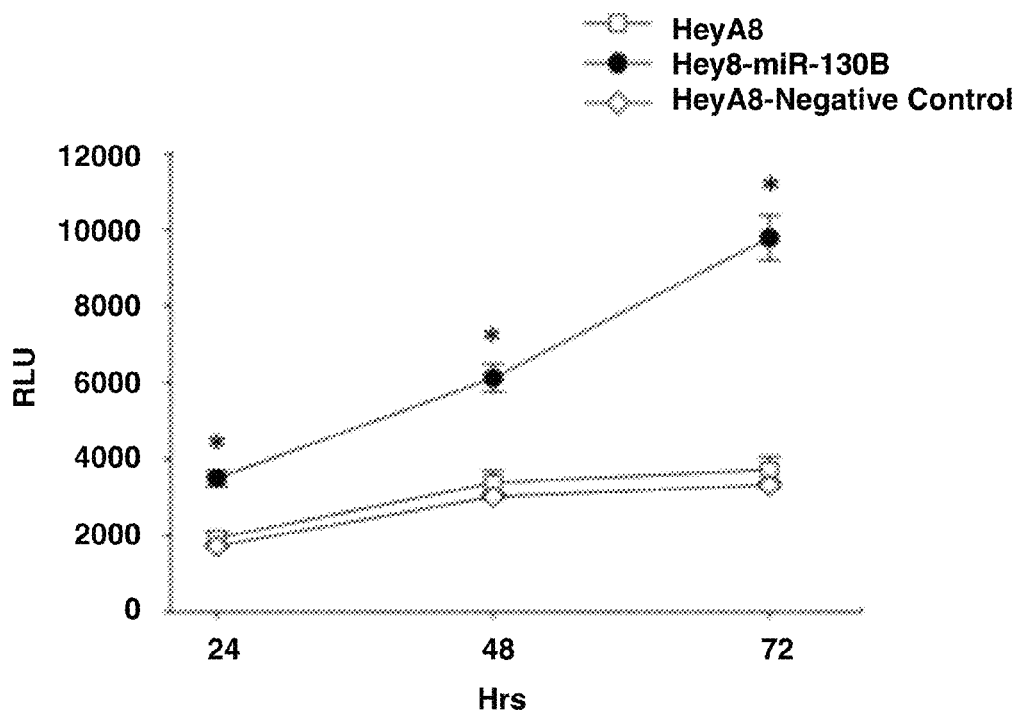
Figure 1C:
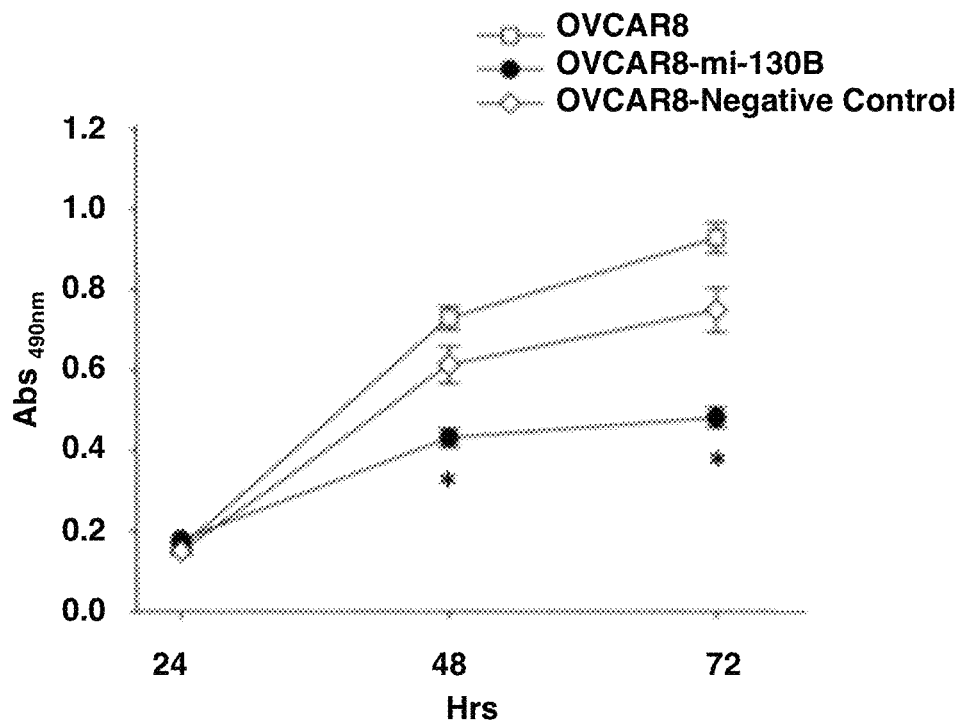
Figure 1D:
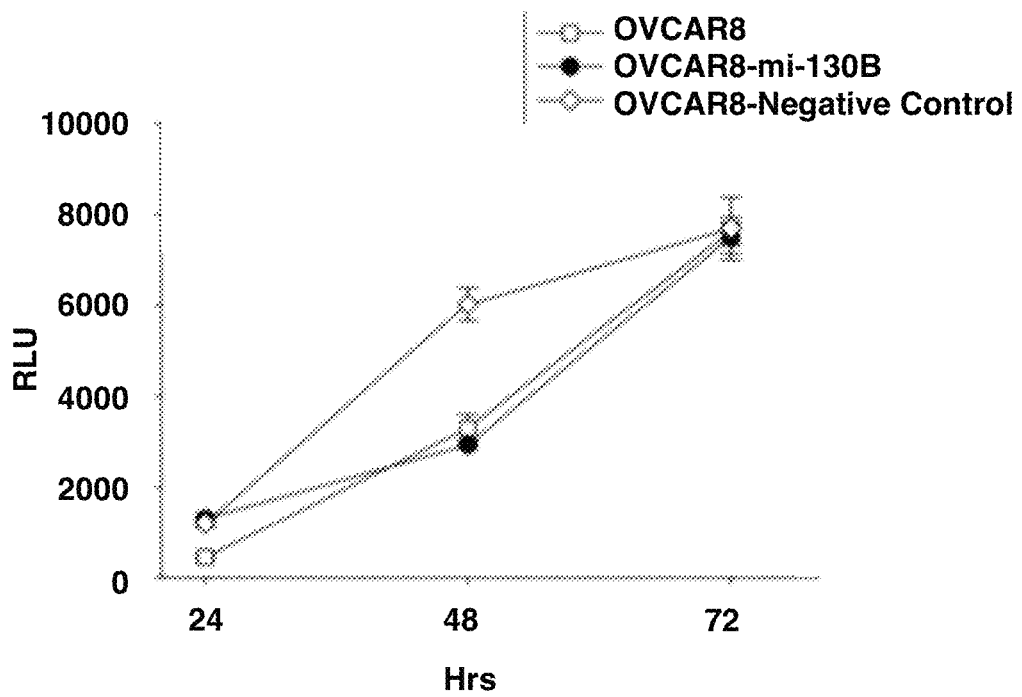
Figure 2A:
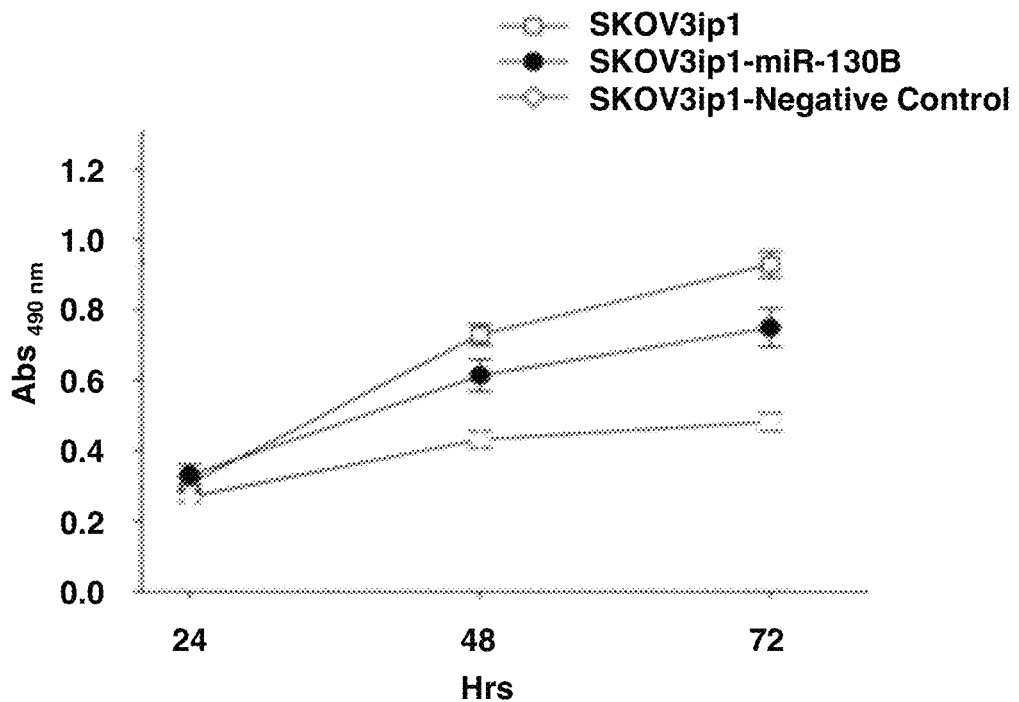
FIGS. 2A-2D: Impact of miR-130b on CDKN2A/p53 deficient ovarian cancer cell lines. The CDKN2A-deficient cell lines OV-90 (FIGS. 2A-2B) and SKov3lp1 (FIG. 2C-2D) were employed to examine the role of CDKN2A (INK4A/ARF) in miR-130b function.
Figure 2B:
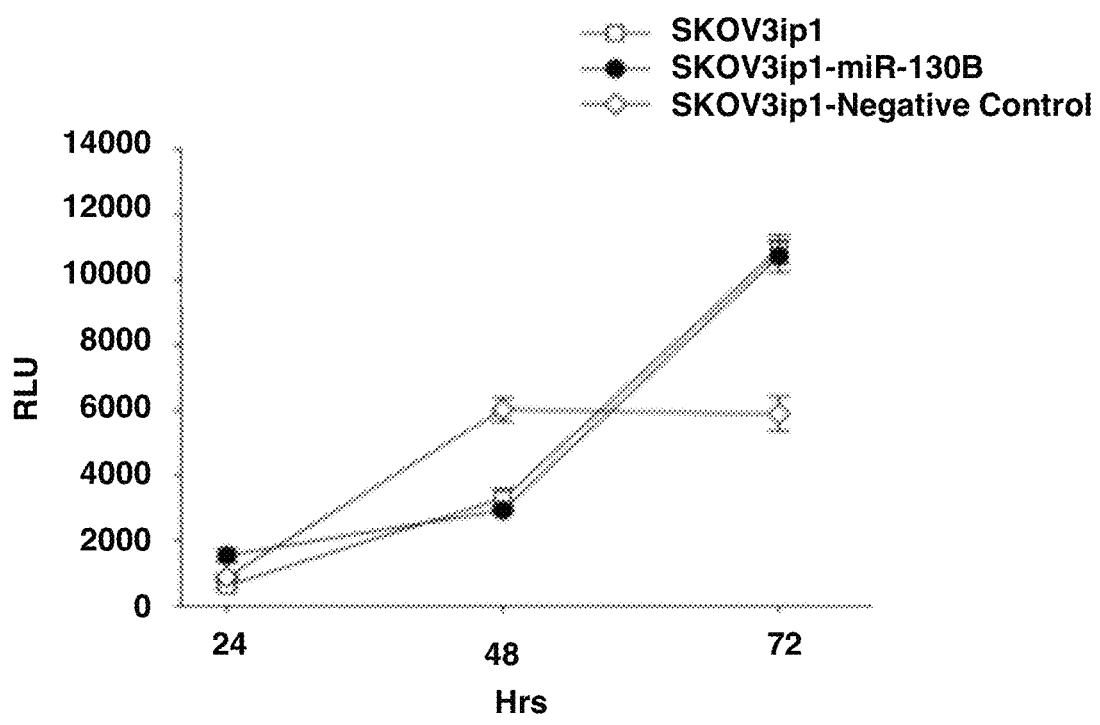
Figure 2C:
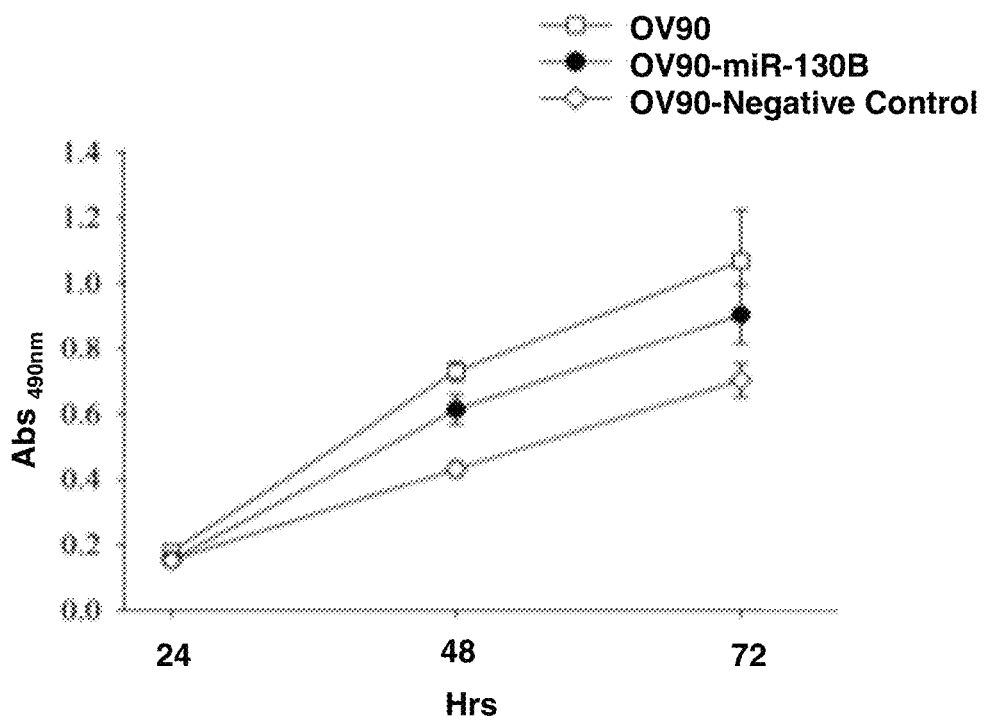
Figure 2D:
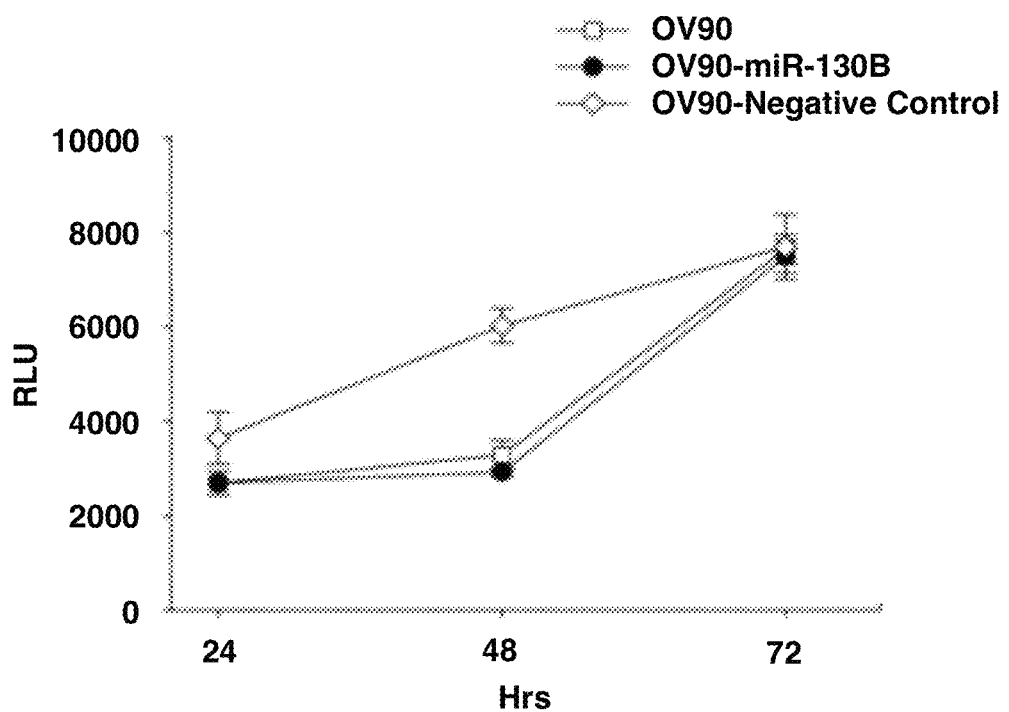

As shown in FIGS. 1A and 1C, HeyA8 cells, which are CDKN2A$^+$ and p53$^+$ demonstrated a robust increase in Caspase 3/7 expression in response to miR-130b. OVCAR8 cells, which are CDKN2A$^+$ and p53$^{mut}$, showed a substantial decrease in proliferation when miR-130b was over-expressed and no effect on apoptosis (FIGS. 1B, 1D). In addition, two CDKN2A-deficient cell lines OV-90 (CDKN2A$^{mut}$ and p53$^{mut}$) and SKOV3ip1 (CDKN2A$^-$ and p53$^{+/-}$) are resistant to miR-130b-mediated inhibition of cell proliferation and miR-130b-driven increase in apoptosis (FIGS. 2A-2D). In all cases, cell proliferation and apoptosis of parental lines treated were not significantly different from the parental control cells treated with NC. Thus, miR-130b is a tumor suppressor of human serous ovarian cancers and whereas its effect on cell proliferation is dependent on the wild type function of CDKN2A its effect on apoptosis depends on the wild type functions of CDKN2A and p53.

EXAMPLE 14 miR-130b is Able to Suppress Tumor Growth and Burden In Vivo

Figure 3B:
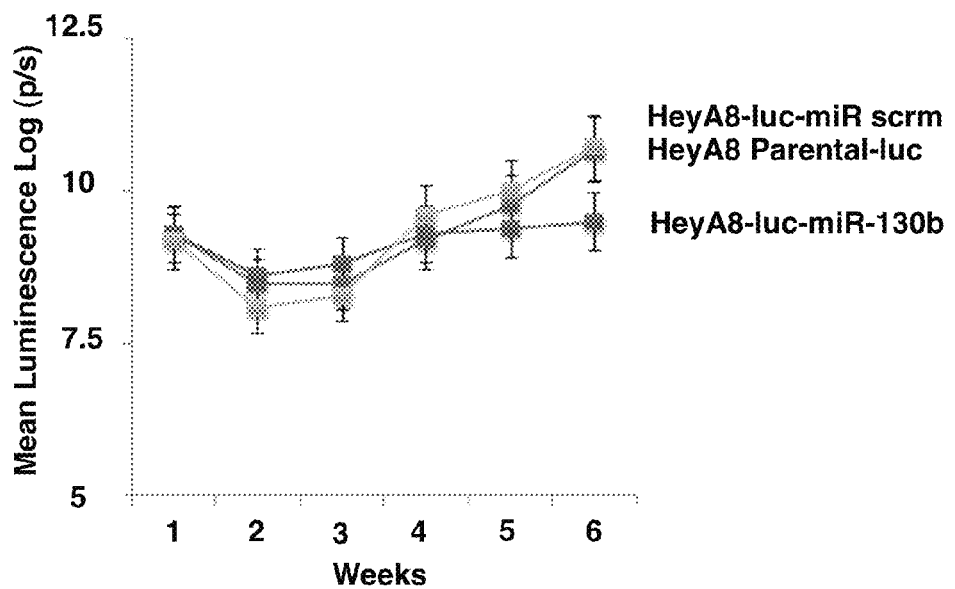
Figure 3C:
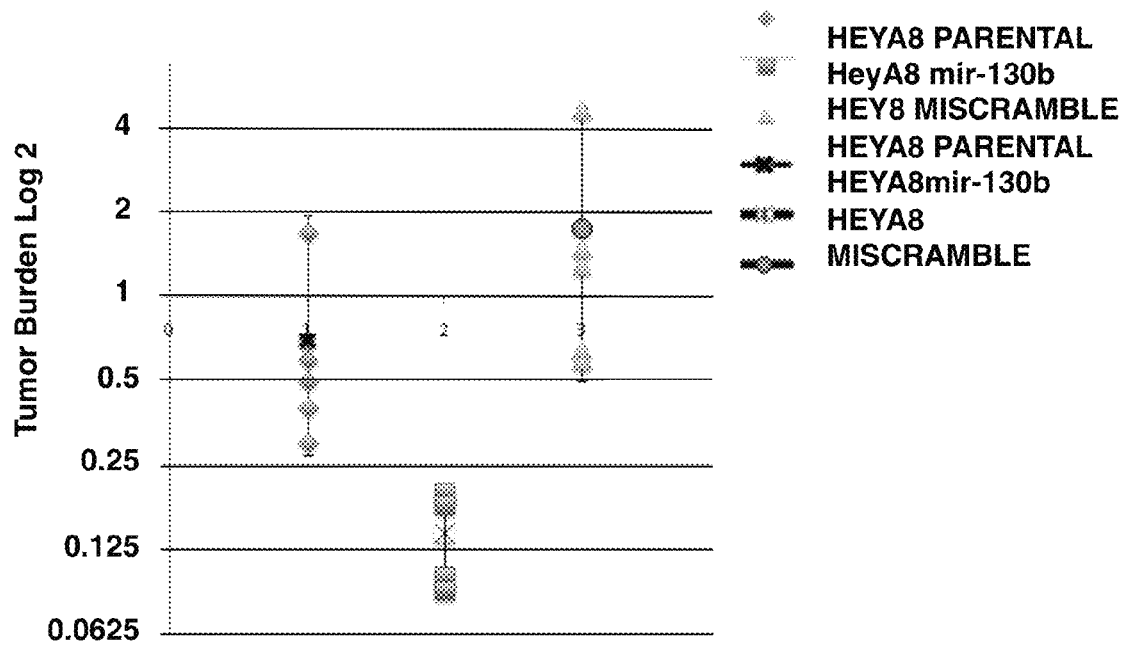

To characterize miR-130b's functional impact in vivo, stable luciferase (luc) clones from HeyA8 cells expressing either miR-130b or NC were generated. Three groups, HeyA8-luc, HeyA8-miR-130b-luc, or HeyA8-NC-luc, consisting of 5 female, (CrTac: NCr-Foxnlnu) nude mice (between 6-8 weeks old) per group were used. All mice were xenografted by intraperitoneal (IP) injection of 2×10$^6$ cells. Mice were monitored weekly through in vivo imaging and the relative progression of tumors over-expressing miR-130b as compared to controls were followed. HeyA8-miR-130b-luc mice showed a significantly decreased tumor progression as compared to parental HeyA8-luc and HeyA8-SCR-luc controls (FIG. 3A). Six weeks after initial IP injection, all mice were sacrificed and tumors excised and weighed ex vivo. Tumor burdens from HeyA8 with miR-130b were 79.9% and 91% smaller than HeyA8 and HeyA8 stably expressing SCR respectively (FIG. 3C). Another interesting observation was the overall invasiveness of the miR-130b xenografts was much less than the control tumors. When removing the tumor masses from the mice, the SCR and HeyA8 parental groups had tumor metastasis throughout the abdominal cavities and bowels (FIG. 3B). The miR-130b group's tumors were generally localized as a single mass near the injection site (FIG. 3B).

EXAMPLE 15 miR-130b can Sensitize p53-Wild Type HeyA8 to Cisplatin

Refractory disease that results from resistance to chemotherapy is a major problem for many ovarian cancer patients. The chemotherapy drug, cisplatin, works by intercalating the genomic DNA of tumor cells causing massive DNA damage that in turn causes the cells to undergo apoptosis or programmed cell death (Dania) 2007; Degterev et al. 2003). However, many patients are resistant to treatments such as cisplatin due to the loss of functional p53. To examine whether the acquired cisplatin resistance can be reversed by miR-130b, HeyA8 cells were transfected with a miR-130b mimic or a negative miRNA control and then treated with cisplatin. Seventy-two hours following cisplatin treatment, proliferation and caspase activity were measured using the same MTS and Caspase 3/7 assays used previously. The estimated IC$_{50s}$ for cisplatin for each condition are shown in FIG. 4A. The approximate cisplatin IC$_{50s\,for}$ HeyA8 with the NC and miR-130b were 18.3 µg/mL and 9.9 µg/mL respectively.

In the presence of miR-130b, the concentration of cisplatin needed to reach 50% viability was an estimated 53% less compared to the negative control. FIG. 4B shows the caspase activity with respect to cisplatin-induced apoptosis. The caspase activation was significantly enhanced in HeyA8 cells over expressing miR-130b correlating with an increase in apoptosis. These results indicate that miR-130b not only functions as a tumor suppressor but can also increase the sensitivity to platinum-based chemotherapy.

EXAMPLE 16 miR-130b Selectively Induces the p53 Pathway in the p53-Wild Type Background and the p63 Pathway in the p53-Mutant Background Recently, p63 was reported to be a direct transcriptional activator of miR-130b and Dicer, a key enzyme for miRNA biogenesis (Su et al. 2010). In addition p63-mediated up regulation of both miR-130b and Dicer is able to significantly decrease the metastatic potential of p53$^{-/-}$; p63$^{-/-}$ and p53$^{-/-}$; p63$^{+/-}$ osteosarcomas, lung adenocarcinomas and mammary adenocarcinomas (Su et al. 2010). To elucidate the mechanisms underlying miR-130b-mediated inhibition of cell proliferation and increase in apoptosis the levels of key upstream and downstream target genes in the p63/p53/p73 network were measured.

Figure 5A:
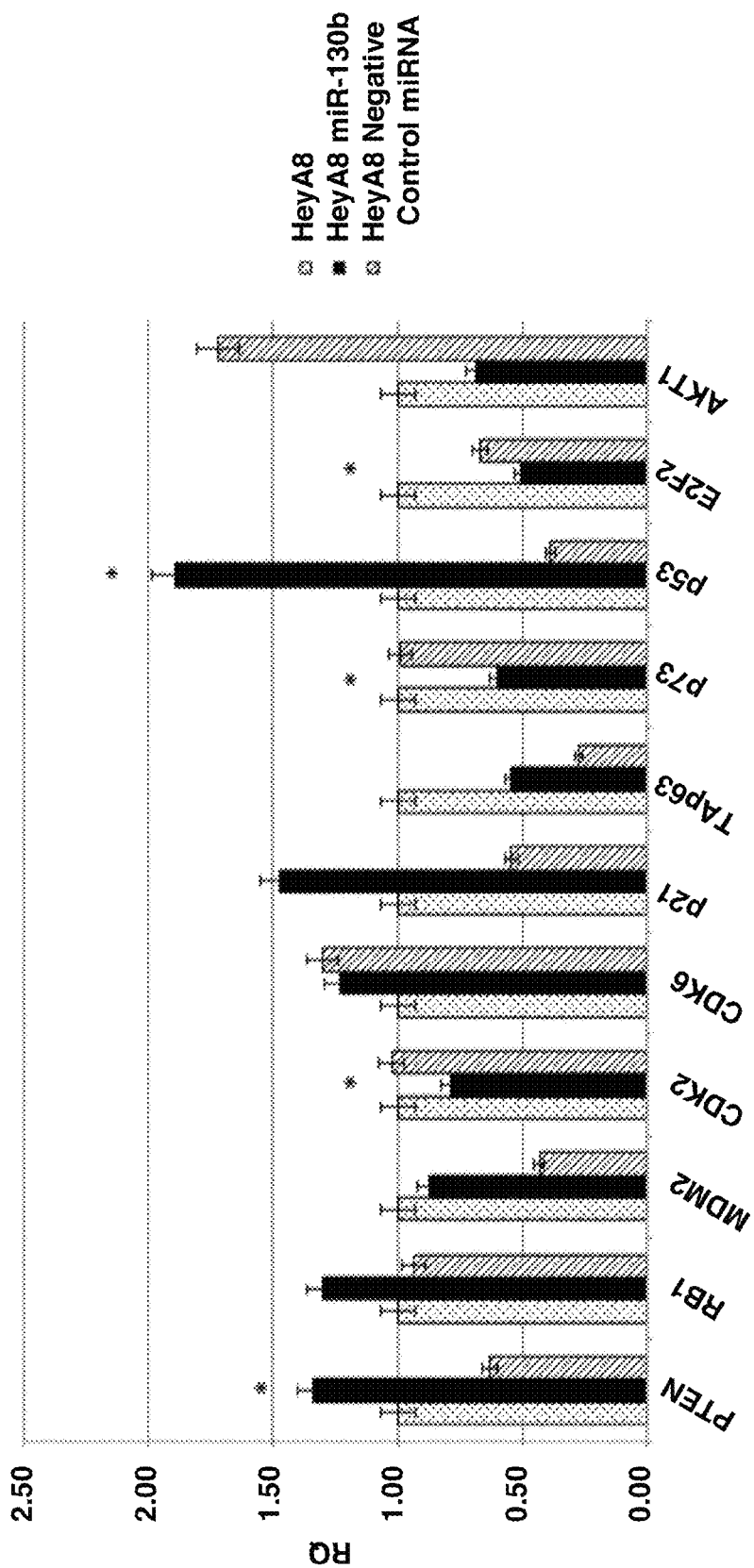
FIGS. 5A-5C: Impact of miR-130b on patterns of gene expression. A panel of genes was used that are associated with the p53 family that functions to control cell proliferation and apoptosis downstream of p53. Quantitative RT-PCR assays using SYBR green were used to measure the relative changes in gene expression in HEYA8 (FIGS. 5A-5B) and OVCAR8 (FIG. 5C) in response to miR130b as compared to the parental strain and the same cell lines transfected with a negative control miRNA.
Figure 5B:
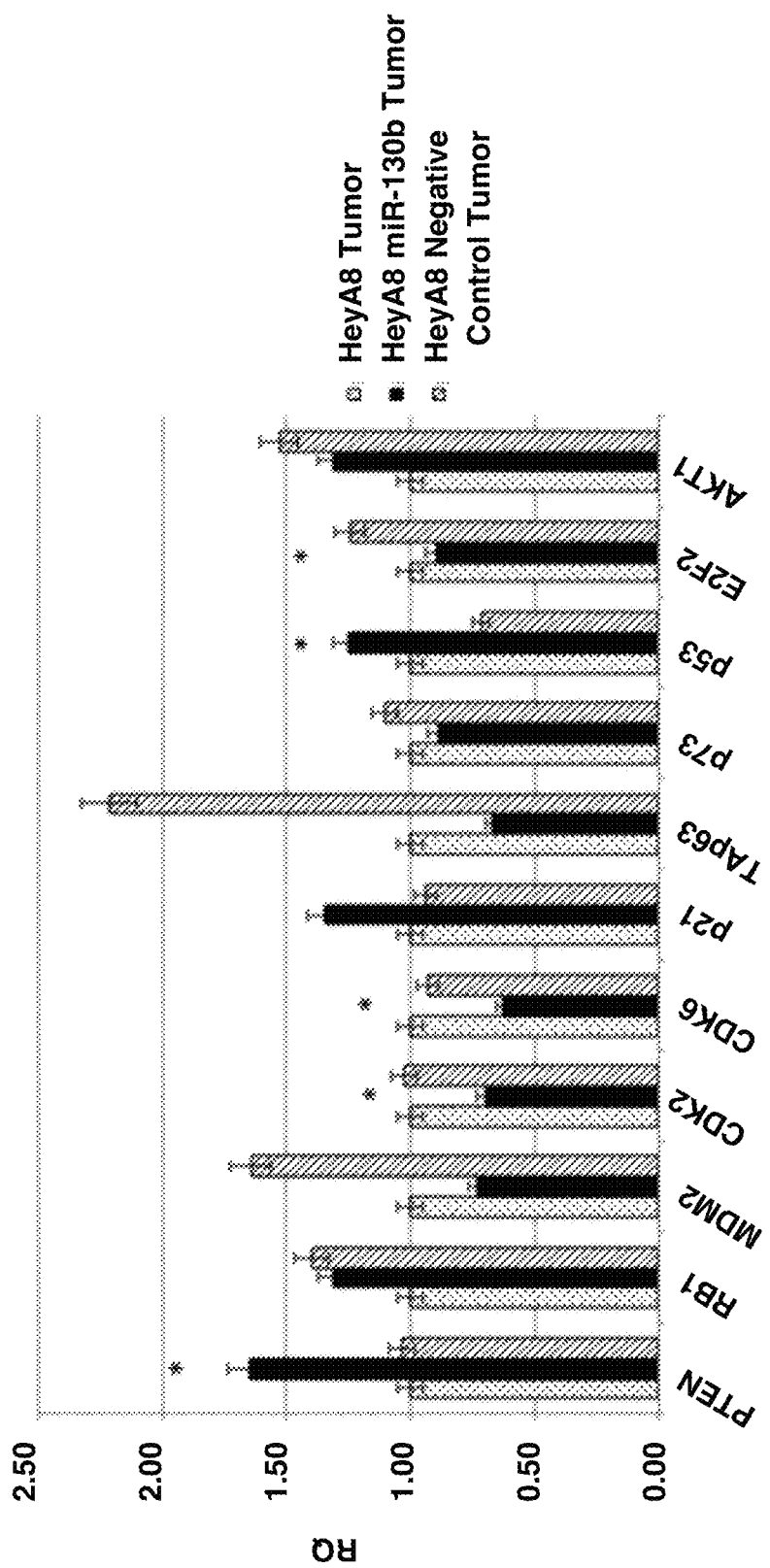
Figure 5C:
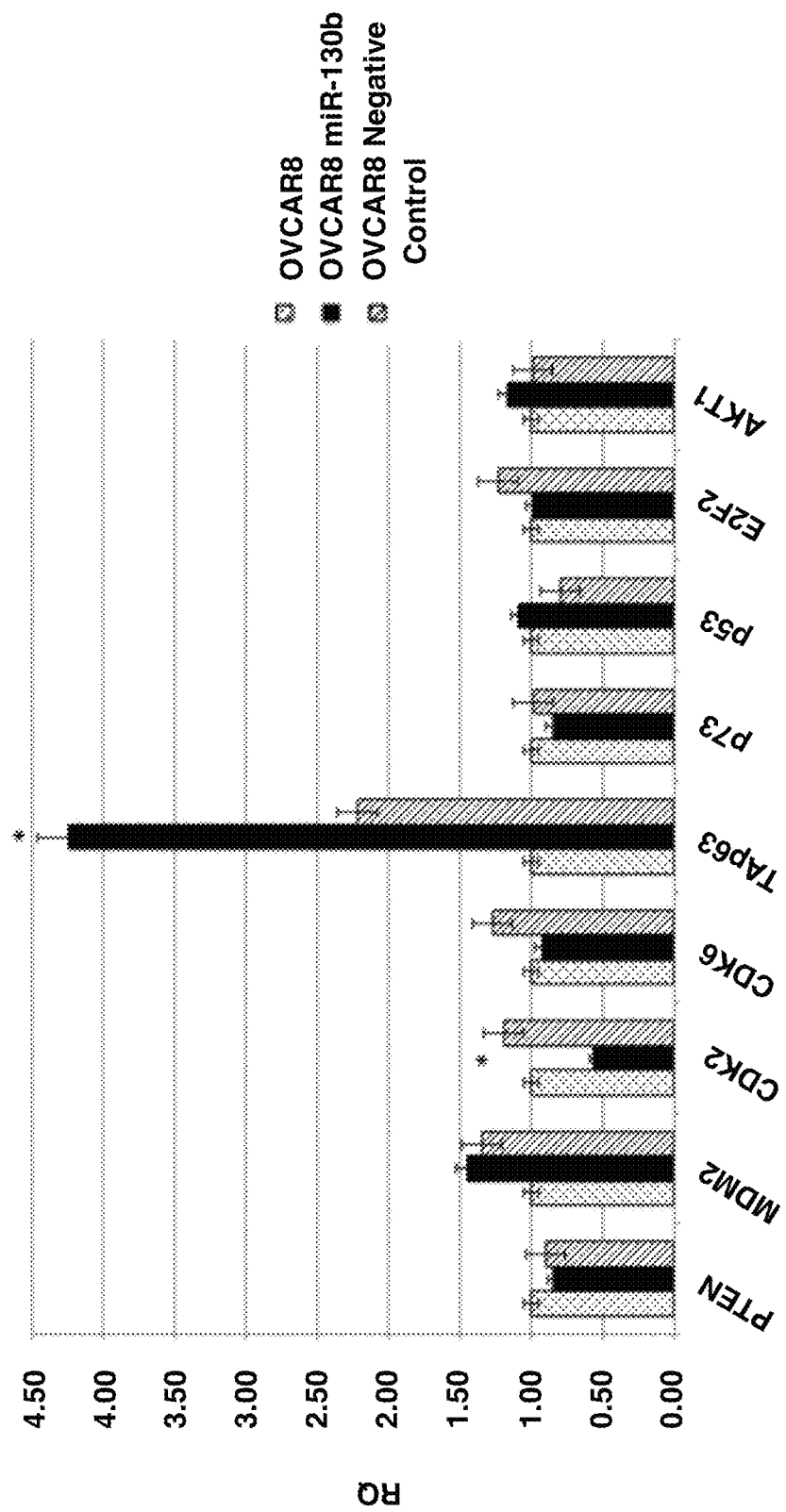

From data shown in FIGS. 5A-5C, three pathways that are likely to underlie the distinct impacts of miR-130b on p53-wildtype, p53-deficient and p53-mutant ovarian cancers are revealed. In the presence of wild type p53 (HeyA8), miR-130b appears to enhance p53 action by increasing the levels of p53 and other tumor suppressors PTEN, p21 and RB1 and decrease levels of the p53-feedback inhibitors δNp73. One of the ultimate outcomes is the down regulation of E2F2, a potent activator of cell proliferation that is often inappropriately activated in cancer cells. Thus, miR130b amplifies the effects of p53 to exert its actions via the p14ARF/mdm2/p53 pathway and also utilizes the PTEN pathway to act as a tumor suppressor in p53-wild type ovarian cancers. In the p53-mutant OVCAR8 cell line, miR-130b has no effect on any of the above genes and instead up-regulates p63. Mutant-p53 acts, therefore, as a dominant negative suppressor of p53 of the p14ARF/mdm2/p53 pathway. In this background miR-130b may act to compensate for the loss of p53 by amplifying its upstream transcriptional activator p63 through a self-reinforcing feed forward loop. miR-130b exerts its effects through p16INK4/Cyclin D/CDK4/6 to activate RB1. Indeed miR-130b is seen to up regulate RB1 (FIG. 5C) and PTEN suggesting that the PTEN pathway may act synergistically with the p63 pathway to mediate miR-130b driven tumor suppression.

Figure 6A:
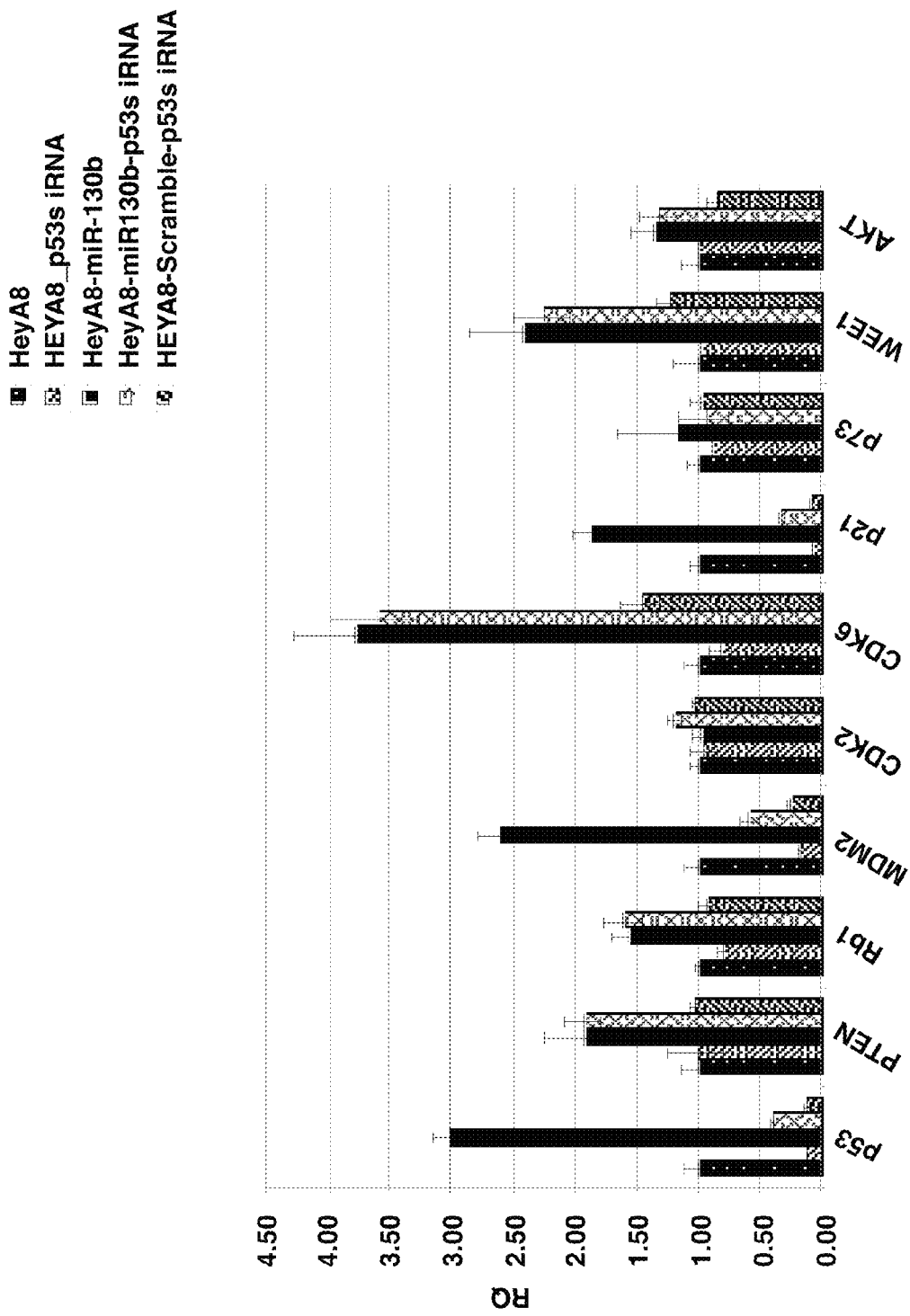
FIGS. 6A-6B: Impact of siRNA against p53 on miR-130b-regulated patterns of gene expression. Since many of the up regulated genes that were induced by miR-130b were also downstream transcriptional targets of p53, transient, siRNA knockdown of p53 was used with and without miR-130b present in HeyA8 (FIG. 6A) and OVCAR8 (FIG. 6B) cells and used qPCR to measure our gene set again with respect to p53. The goal was to dissect the p53-dependent and independent impacts of miR-130b in the p53-wild type HeyA8.
Figure 6B:
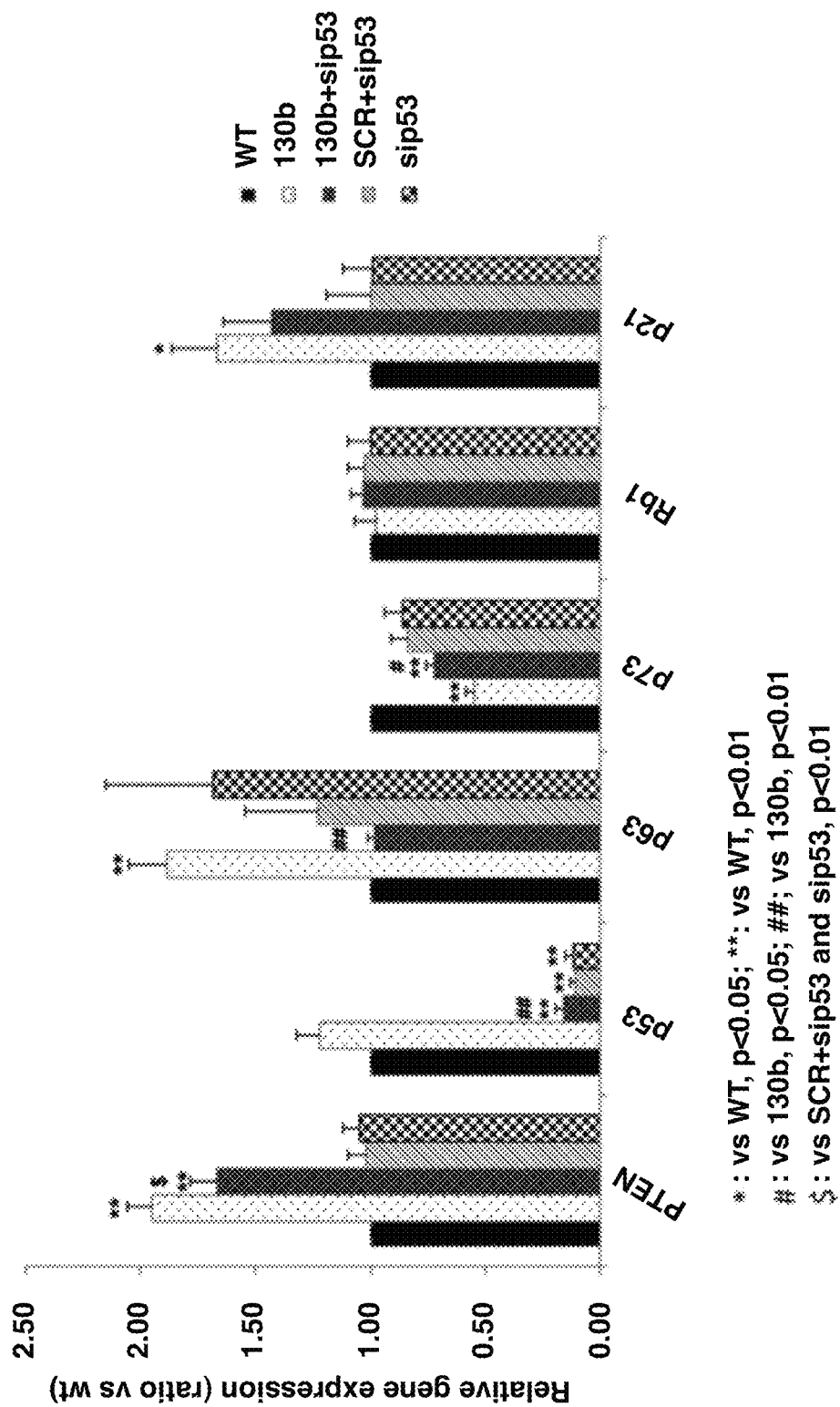

To determine which of these gene expression changes are dependent on p53 patterns of gene expression in miR-130b over-expressing HeyA8 cells were compared in the presence of a siRNA to p53 (siP53). These siRNA studies revealed further complexity in relation to the p53/p63/p73 axis. First, siP53 down-regulated p53, MDM2, p21 and up-regulated RB1 (FIG. 6A). These data suggest that wild type p53 directly or indirectly induces p53, MDM2 and p21 and represses RB1 all of which are up regulated by miR-130b. miR-130b-mediated induction of p53, mdm2 and p21 and repression of δNp73 is reversed by siP53 and therefore dependent on p53 (FIG. 6A). miR-130b-mediated up-regulation of RB1 is further enhanced by siP53 and therefore is also indirectly dependent on p53 (FIG. 6A). By contrast, miR-130b driven increase in PTEN is independent of p53 (FIG. 6A). In OVCAR8 miR-130b driven up regulation of PTEN and p63 is reversed by siP53 suggesting that this feed-forward loop whereby, miR-130b activates its' own transcriptional activator p63 in a mutant p53 background is dependent on the gain of function mutation that is associated with OVCAR8 cells.

The present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered or modified and all such variations are considered within the scope and spirit of the present invention. Also, the terms in the claims have their plain, ordinary meaning unless otherwise explicitly and clearly defined by the patentee.

What is claimed is:

1. A method of improving a therapeutic response to an ovarian cancer treatment in a subject, comprising the step of administering an effective amount of microRNA-130b, double-stranded RNA which mimics mature endogenous micro-RNA-130b, or an oligonucleotide based pre-microRNA-130b drug to suppress the growth of the ovarian cancer or to increase sensitivity of the ovarian cancer to the treatment, thereby improving the therapeutic response.

2. The method of claim 1, whereby said oligonucleotide based pre-microRNA-130b drug is selected from the group consisting of single-stranded oligonucleotide based pre-microRNA-130b drug and double-stranded oligonucleotide based pre-microRNA-130b drug.

3. The method of claim 1, whereby said ovarian cancer is epithelial ovarian cancer.

4. The method of claim 1, whereby said therapeutic response comprises treating with radiation, carboplatin, cisplatin, paclitaxel, an alkylating agent, an antimetabolite, an antitumor antibiotic and a DNA topoisomerase inhibitor.

5. A method of treating an ovarian cancer in a subject in need of such treatment comprising the step of administering an effective amount of microRNA-130b, double-stranded RNA which mimics mature endogenous micro-RNA-130b, or an oligonucleotide based pre-microRNA-130b drug to suppress cell proliferation in the ovarian cancer, thereby treating the ovarian cancer in the subject.

6. The method of claim 5, whereby said oligonucleotide based pre-microRNA-130b drug is selected from the group consisting of a single-stranded oligonucleotide based pre-microRNA-130b drug and a double-stranded oligonucleotide based pre-microRNA-130b drug.

7. The method of claim 5, whereby said ovarian cancer is epithelial ovarian cancer.

8. The method of claim 5, further comprising:
   treating said subject with radiation, carboplatin, cisplatin, paclitaxel, an alkylating agent, an antimetabolite, an antitumor antibiotic and a DNA topoisomerase inhibitor.

9. The method of claim 5, wherein said microRNA-130b is administered as a nucleic acid construct encoding an artificial miRNA presented as a double-stranded RNA, a precursor hairpin, a primary miRNA in single stranded RNA form or encoded in a DNA vector delivered in a suitable pharmaceutical carrier.

10. The method of claim 9, wherein said pharmaceutical carrier is selected from the group consisting of a virus, a liposome, and a polymer.

11. The method of claim 5, wherein said microRNA-130b is administered as a nanoparticle, a liposome, a vector or a polymer.

12. The method of claim 11, wherein said vector selected from the group consisting of a plasmid, a cosmid, a phagemid and a virus.

* * * * *